US009086408B2

(12) United States Patent
Egan et al.

(10) Patent No.: US 9,086,408 B2
(45) Date of Patent: Jul. 21, 2015

(54) MULTIANALYTE ASSAY

(75) Inventors: Richard Laswell Egan, Oceanside, CA (US); Graham Peter Lidgard, La Jolla, CA (US); David Dickson Booker, Oceanside, CA (US); Christopher Johann Johnson, San Diego, CA (US); Alexander Belenky, San Diego, CA (US); Stan Vukajlovich, San Diego, CA (US)

(73) Assignee: Nexus Dx, Inc., San Diego, CA (US)

( * ) Notice: Subject to any disclaimer, the term of this patent is extended or adjusted under 35 U.S.C. 154(b) by 1175 days.

(21) Appl. No.: 12/596,835

(22) PCT Filed: Apr. 30, 2008

(86) PCT No.: PCT/US2008/062088
§ 371 (c)(1),
(2), (4) Date: May 17, 2010

(87) PCT Pub. No.: WO2009/014787
PCT Pub. Date: Jan. 29, 2009

(65) Prior Publication Data
US 2010/0304359 A1    Dec. 2, 2010

Related U.S. Application Data

(60) Provisional application No. 60/915,051, filed on Apr. 30, 2007.

(51) Int. Cl.
*C12Q 1/70* (2006.01)
*C12M 1/34* (2006.01)
*G01N 33/543* (2006.01)
*B01L 3/02* (2006.01)
*B01L 3/00* (2006.01)

(52) U.S. Cl.
CPC ......... *G01N 33/54366* (2013.01); *B01L 3/0272* (2013.01); *B01L 3/5023* (2013.01); *B01L 3/5029* (2013.01)

(58) Field of Classification Search
None
See application file for complete search history.

(56) References Cited

U.S. PATENT DOCUMENTS

| | | | |
|---|---|---|---|
| 4,235,601 A | 11/1980 | Deutsch et al. | |
| 4,275,149 A | 6/1981 | Litman et al. | |
| 4,299,916 A | 11/1981 | Litman et al. | |
| 4,366,241 A | 12/1982 | Tom et al. | |
| 4,703,017 A | 10/1987 | Campbell et al. | |
| 4,806,311 A | 2/1989 | Greenquist | |
| 4,816,567 A | 3/1989 | Cabilly et al. | |
| 4,818,677 A | 4/1989 | Hay-Kaufman et al. | |
| 4,943,522 A | 7/1990 | Eisinger et al. | |
| 5,073,341 A * | 12/1991 | Hargreaves | 422/401 |
| 5,075,078 A | 12/1991 | Osikowicz et al. | |
| 5,096,809 A | 3/1992 | Chen et al. | |
| 5,096,837 A | 3/1992 | Fan et al. | |
| 5,118,428 A | 6/1992 | Sand et al. | |
| 5,118,630 A | 6/1992 | Glaze | |
| 5,221,616 A | 6/1993 | Kolb et al. | |
| 5,223,220 A | 6/1993 | Fan et al. | |
| 5,225,328 A | 7/1993 | Chang | |
| 5,270,163 A | 12/1993 | Gold et al. | |
| 5,415,994 A | 5/1995 | Imrich et al. | |
| 5,434,057 A | 7/1995 | Dorian | |
| 5,475,096 A | 12/1995 | Gold et al. | |
| 5,508,178 A | 4/1996 | Rose et al. | |
| 5,521,102 A | 5/1996 | Boehringer et al. | |
| RE35,306 E | 7/1996 | Chen et al. | |
| 5,536,646 A | 7/1996 | Sand et al. | |
| 5,541,069 A | 7/1996 | Mortensen et al. | |
| 5,559,041 A | 9/1996 | Kang et al. | |
| 5,605,894 A | 2/1997 | Blank et al. | |
| 5,686,315 A | 11/1997 | Pronovost et al. | |
| 5,712,172 A | 1/1998 | Huang et al. | |
| 5,763,262 A | 6/1998 | Wong et al. | |
| 5,766,961 A | 6/1998 | Pawlak et al. | |
| 5,770,460 A | 6/1998 | Pawlak et al. | |
| 5,773,234 A | 6/1998 | Pronovost et al. | |
| 5,786,220 A | 7/1998 | Pronovost et al. | |
| 5,804,452 A | 9/1998 | Pronovost et al. | |
| 5,814,455 A | 9/1998 | Pronovost et al. | |
| 5,837,466 A | 11/1998 | Lane et al. | |
| 5,939,331 A | 8/1999 | Burd et al. | |
| 6,028,055 A | 2/2000 | Lowe et al. | |
| 6,187,598 B1 | 2/2001 | May et al. | |
| 6,207,392 B1 | 3/2001 | Weiss et al. | |
| 6,306,642 B1 | 10/2001 | Nelson et al. | |
| 6,352,862 B1 | 3/2002 | Davis et al. | |
| 6,485,982 B1 | 11/2002 | Charlton | |
| 6,534,320 B2 | 3/2003 | Ching et al. | |
| 6,709,818 B1 | 3/2004 | Nelson et al. | |

(Continued)

FOREIGN PATENT DOCUMENTS

| | | |
|---|---|---|
| JP | 2003507714 | 2/2003 |
| JP | 2004508541 | 3/2004 |

(Continued)

OTHER PUBLICATIONS

Cazacu et al. (Journal of Clinical Microbiology. 2004; 42 (8): 3661-3664).*
Maeda et al. (Journal of Bioluminescence and Chemiluminescence. 1989; 4: 140-148).*
Written Opinion of the International Searching Authority for International Application No. PCT/2008/062088, dated Jun. 30, 2009.
Clinical Chemistry, vol. 47(10); 1885-1893 (2001).
J. Biochem. vol. 110(4):486-492 (1991).
European Search Report Issued in EP08826586.3 on Mar. 24, 2010.
Anonymous, "Detergents," pp. 1-6, 2003. Retrieved from internet: URL:http://wolfson.huji.ac.il/purification/PDF/detergents/CALBIOCHEM-DetergentsIII.pdf Retrieved on Mar. 24, 2010.

(Continued)

*Primary Examiner* — Shanon A Foley
(74) *Attorney, Agent, or Firm* — Knobbe, Martens, Olson & Bear, LLP

(57) ABSTRACT

The invention provides compositions, systems and methods for detecting multiple analytes from a sample.

22 Claims, 8 Drawing Sheets

(56) References Cited

U.S. PATENT DOCUMENTS

| | | | |
|---|---|---|---|
| 6,719,691 B2 | 4/2004 | Kritzman et al. | |
| 6,767,714 B2 | 7/2004 | Nazareth et al. | |
| 6,790,611 B2 | 9/2004 | Lassen et al. | |
| 6,946,546 B2 | 9/2005 | Vaughan et al. | |
| 6,967,250 B1 | 11/2005 | Kumar et al. | |
| 6,984,491 B2 | 1/2006 | Mirkin et al. | |
| 7,022,492 B2 | 4/2006 | Zheng et al. | |
| 7,022,529 B2 | 4/2006 | Singh et al. | |
| 7,026,120 B2 | 4/2006 | Hayden | |
| 7,026,135 B2 | 4/2006 | Price-Jones et al. | |
| 7,033,781 B1 | 4/2006 | Short | |
| 7,052,854 B2 | 5/2006 | Melker et al. | |
| 7,052,916 B2 | 5/2006 | Johnson | |
| 7,056,679 B2 | 6/2006 | Pillutla et al. | |
| 7,070,945 B2 | 7/2006 | Jackowski et al. | |
| 7,101,667 B2 | 9/2006 | Imperiali et al. | |
| 7,223,542 B2 | 5/2007 | Raitano et al. | |
| 7,262,290 B2 | 8/2007 | Berrettini | |
| 7,332,569 B2 | 2/2008 | Cojocaru et al. | |
| 7,348,149 B2 | 3/2008 | Feder et al. | |
| 7,361,473 B2 | 4/2008 | Valkirs et al. | |
| 7,932,099 B2 | 4/2011 | Egan | |
| 2003/0049167 A1 | 3/2003 | Jerome et al. | |
| 2003/0108918 A1* | 6/2003 | Castor et al. | 435/6 |
| 2003/0157699 A1 | 8/2003 | Jerome et al. | |
| 2004/0018504 A1* | 1/2004 | Bjorn et al. | 435/6 |
| 2004/0197793 A1* | 10/2004 | Hassibi et al. | 435/6 |
| 2004/0237674 A1* | 12/2004 | Wu et al. | 73/864 |
| 2006/0169708 A1* | 8/2006 | Chang | 220/826 |
| 2009/0061417 A1* | 3/2009 | Inoue | 435/5 |

FOREIGN PATENT DOCUMENTS

| | | |
|---|---|---|
| JP | 2007-046959 | 2/2007 |
| JP | 2007046959 | 2/2007 |
| JP | 2007537428 | 12/2007 |
| WO | WO2005/072055 | 8/2005 |
| WO | WO2007/098184 | 8/2007 |

OTHER PUBLICATIONS

Brennan, et al., "Preparation of bispecific antibodies by chemical recombination of monoclonal immunoglobulin G1 fragments." Science 229:81-83 (1985).

Brodeur et al., Monoclonal Antibody Production Techniques and Applications, pp. 51-63, Marcel Dekker, Inc., New York, 1987.

Carter et al., "High level escherichia coli expression and production of a bivalent humanized antibody fragment," Bio/Technology, 10:163-167 (1992).

Clark, Mike. "Antibody humanization: a case of the 'Emperor's new clothes'?." Immunology today 21.8:397-402 (2000).

Coligan, John E., et al., Current Protocols in Immunology, vol. 1-6 (eds. 1999).

Coding, Monoclonal Antibodies: Principles and Practice, pp. 59-103, Academic Press, 1996.

Hudson, Peter J. "Recombinant antibody constructs in cancer therapy." Current opinion in immunology 11.5:548-557 (1999).

Huhtinen, et al. "Quantitative, rapid europium (III) nanoparticle-label-based all-in-one dry—reagent immunoassay for thyroid—stimulating hormone." Clinical chemistry 50.10:1935-1936 (2004).

Jones, Peter T., et al. "Replacing the complementarity—determining regions in a human antibody with those from a mouse." Nature 321:522-525 (1986).

Köhler, et al., "Continuous cultures of fused cells secreting antibody of predefined specificity." Nature 256:495-497 (1975).

Kozbor, et al., "A human hybrid myeloma for production of human monoclonal antibodies," The Journal of Immunology 133.6:3001-3005 (1984).

Little, M., et al. "Of mice and men: hybridoma and recombinant antibodies." Immunology today 21.8:364-370 (2000).

Morimoto, et al., "Single-step purification of F (ab') 2 fragments of mouse monoclonal antibodies (immunoglobulins G1) by hydrophobic interaction high performance liquid chromatography using TSKgel Phenyl-5PW," Journal of Biochemical and Biophysical Methods, 24:107-117 (1992).

Morrison et al., Proc. Natl. Acad. Sci. USA, 81:6851 6855 (1984)

Morrison, et al. "Chimeric human antibody molecules: Mouse antigen-binding domains with human constant region domains." Proceedings of the National Academy of Sciences 81.21:6851-6855 (1984).

Munson, et al., "Ligand: a versatile computerized approach for characterization of ligand-binding systems." Analytical biochemistry 107:220-239 (1980).

Presta L.G., "Antibody engineering." Curr. Op. Struct. Biol., 2:593-596 (1992).

Richardson F. S., "Terbium(III) and Europium(III) Ions as Luminescent probes and Stains for Biomolecular Systems," Chem. Rev., 82:541-552 (1982).

Riechmann, et al., "Reshaping human antibodies for therapy," Nature 332:323-327 (1988).

Extended European Search Report in EP08826586.3 mailed May 7, 2010.

Communication pursuant to Article 94(3) EPC received in Application No. 08 826-586.3-1408, mailed Mar. 6, 2015.

* cited by examiner

SEQUENCE LISTING

<160> NUMBER OF SEQ ID NOS: 6

<210> SEQ ID NO 1
<211> LENGTH: 10
<212> TYPE: DNA
<213> ORGANISM: Unknown
<220> FEATURE:
<223> OTHER INFORMATION: Pyranosyl RNA capture moiety 102a10-3-NH2
<220> FEATURE:
<221> NAME/KEY: misc_feature
<222> LOCATION: (1)..(10)
<223> OTHER INFORMATION: Residues are 4'-2' pyranosyl RNA

<400> SEQUENCE: 1
tagaacgaag 10

<210> SEQ ID NO 2
<211> LENGTH: 10
<212> TYPE: DNA
<213> ORGANISM: Unknown
<220> FEATURE:
<223> OTHER INFORMATION: Pyranosyl RNA capture moiety 102b10-3-NH2
<220> FEATURE:
<221> NAME/KEY: misc_feature
<222> LOCATION: (1)..(10)
<223> OTHER INFORMATION: Residues are 4'-2' pyranosyl RNA

<400> SEQUENCE: 2

```
cttcgttcta                                                                    10

<210> SEQ ID NO 3
<211> LENGTH: 10
<212> TYPE: DNA
<213> ORGANISM: Unknown
<220> FEATURE:
<223> OTHER INFORMATION: Pyranosyl RNA capture moiety 119a10-1-NH2
<220> FEATURE:
<221> NAME/KEY: misc_feature
<222> LOCATION: (1)..(10)
<223> OTHER INFORMATION: Residues are 4'-2' pyranosyl RNA

<400> SEQUENCE: 3
tcagtggatg                                                                    10

<210> SEQ ID NO 4
<211> LENGTH: 10
<212> TYPE: DNA
<213> ORGANISM: Unknown
<220> FEATURE:
<223> OTHER INFORMATION: Pyranosyl RNA capture moiety 119b10-1-NH2
<220> FEATURE:
<221> NAME/KEY: misc_feature
<222> LOCATION: (1)..(10)
<223> OTHER INFORMATION: Residues are 4'-2' pyranosyl RNA

<400> SEQUENCE: 4
catccactga                                                                    10

<210> SEQ ID NO 5
<211> LENGTH: 10
<212> TYPE: DNA
<213> ORGANISM: Unknown
<220> FEATURE:
<223> OTHER INFORMATION: Pyranosyl RNA capture moiety 3a10-1-NH2
<220> FEATURE:
<221> NAME/KEY: misc_feature
<222> LOCATION: (1)..(10)
<223> OTHER INFORMATION: Residues are 4'-2' pyranosyl RNA

<400> SEQUENCE: 5
gtattgcgag                                                                    10

<210> SEQ ID NO 6
<211> LENGTH: 10
<212> TYPE: DNA
<213> ORGANISM: Unknown
<220> FEATURE:
<223> OTHER INFORMATION: Pyranosyl RNA capture moiety 3b10-1-NH2
<220> FEATURE:
<221> NAME/KEY: misc_feature
<222> LOCATION: (1)..(10)
<223> OTHER INFORMATION: Residues are 4'-2' pyranosyl RNA

<400> SEQUENCE: 6
ctcgcaatac                                                                    10
```

MULTIANALYTE ASSAY

CROSS-REFERENCE

This Application is a national stage application of PCT/U.S.2008/062088 filed Apr. 30, 2008, which claims the benefit of priority to U.S. Provisional Application Ser. No. 60/915,051, which was filed Apr. 30, 2007 and is incorporated herein in its entirety. This application is a related to U.S. Application Ser. No. 11/677,559, filed Feb. 21, 2007, which is incorporated herein by reference in its entirety.

STATEMENT AS TO FEDERALLY SPONSORED RESEARCH

This invention was made with the support of the United States government under Contract number 200-2007-19345 Center for Disease Control.

BACKGROUND OF THE INVENTION

While analyte detection device and assays are known in the art, such as those used for diagnostics for infectious diseases, they lack sufficient sensitivity and specificity to detect multiple analytes using a single assay device. A new generation of multianalyte assay devices that are intended for rapid detection of multiple analytes require improved sensitivity and specificity. Therefore, there is a need to develop devices and methods to effectively detect a plurality of analytes and that are capable of minimizing false positive and false negative results, and to often screen samples that contain a mixed pool of target and non-target analytes present in a sample.

SUMMARY OF THE INVENTION

In various aspects of the invention, systems, devices and methods are provided for detection of multiple analytes present in a sample. In one aspect of the invention, devices and processes are provided to provide enhanced sensitivity and specificity to detect a plurality of different analytes in a sample.

In one aspect of the invention, a kit is provided comprising a Sample Collection Device (SCD) and Test Device (TD) configured to provided enhanced sensitivity and specificity for detecting one or more analyte present in a sample. Such samples can contain a mixed pool of non-target and target analytes.

In another aspect of the invention a system is provided for detecting one or more analytes present in a sample which minimizes the steps required to process a sample and simplifies the process for reading a result. Furthermore, the system reduces the level of training required for an operator to process and read results. In one embodiment, the system comprises a SCD, TD and reader.

In yet another aspect methods are provided for detecting one or more analytes present in a sample, comprising administering a sample to devices and systems of the invention, which are configured to provided enhanced detection sensitivity and specificity. In various embodiments, samples screened are from any source and the one or more analytes detected are any entity that is detectable using a detectable entity that binds to an analyte. Analytes include but are not limited to virus or virus components, bacteria or bacterial components, mammalian cell or mammalian cell components, and non-mammalian cell or non-mammalian cell components. For example, in some embodiments the invention provides detection of Influenza types A and B as well as Subtypes of Type A, H1 and H3 and H5.

In a further aspect of the invention, reagents, buffers and immunoassay components are provided, as described herein, which enhance the specificity and sensitivity for detection of multiple analytes if present in the same sample. Such reagents, buffers and immunoassay components include but are not limited to detection probes, capture probes, extraction buffers, antibodies and moieties.

INCORPORATION BY REFERENCE

All publications and patent applications mentioned in this specification are herein incorporated by reference to fie same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A shows the component of the test device; FIG. 5B shows the role of pRNA in the test device.

DETAILED DESCRIPTION OF THE INVENTION

Figure 1:
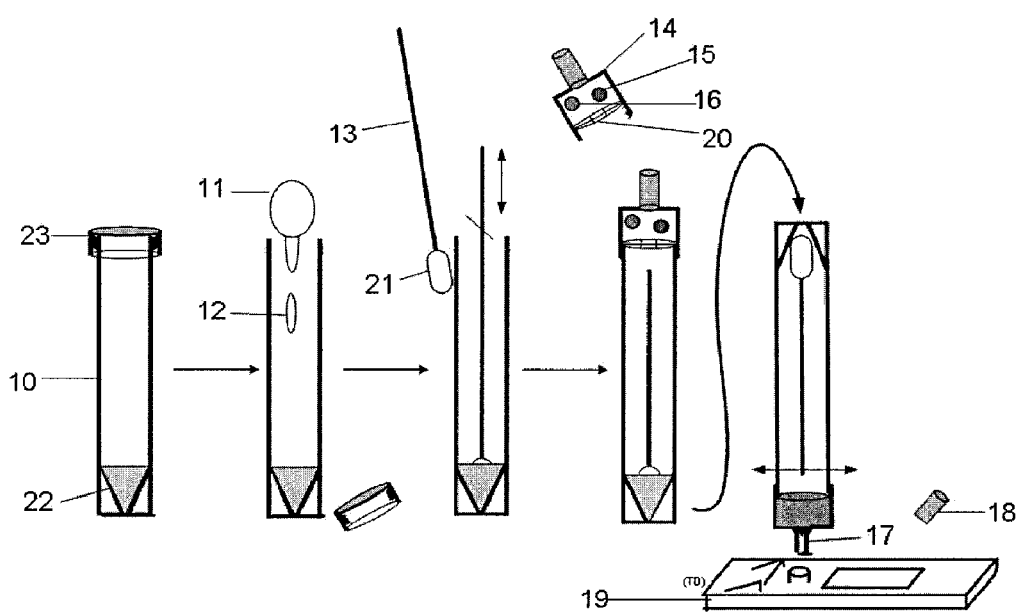
FIG. 1 illustrates an embodiment of sample collection device (SCD).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Additional embodiments for compositions, methods or systems disclosed herein are disclosed in related U.S. patent application Ser. No. 11/677,559.

In one aspect of the invention systems, devices and methods provide a rapid, sensitive process for detecting multiple analytes in a biological sample with high sensitivity and specificity. For example, in some embodiments, an assay is provided which has high sensitivity and fewer false positives than conventional assays. A further embodiment is to provide an apparatus or system for detection of low levels of analytes present in biological samples. In yet another embodiment, an assay system is provided which involves a minimal number of procedural steps, and yields reliable results even when used by untrained persons.

In one embodiment, a system is provided for testing a sample for the presence of a plurality of analytes. Furthermore, detection is in a matter of minutes. In additional embodiments, the invention provide results which are specific and sensitive for one or more target analytes, notwithstanding that results can be read one to several hours after completion of a reaction necessary to obtain a result.

As used herein the term "analyte" or "analytes" refers to the compound or composition to be detected or measured and which has at least one epitope or binding site. The analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair. In other embodiments, one or more analyte detected is an antibody (e.g., IgG, IgM) in a sample (e.g., urine, oral fluid, blood, plasma or serum sample) where the antibody is specific for a virus or virus component, bacteria or bacteria component, cancer cell or tumor antigen. For example, by detecting one or more antibody, the assay indicates that the patient has been previously infected by an infectious agent or suffers an underlying condition with which the antibody is associated. In further embodiments, allergy detection testing comprises detecting the presence of specific IgG, IgM and/or IgE Ab in a subjects oral fluid, whole blood, urine, plasma or serum to specific allergens.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof. A non-exhaustive list of exemplary analytes is set forth in U.S. Pat. No. 4,366,241, at column 19, line 7 through column 26, line 42; U.S. Pat. Nos. 4,299,916; 4,275,149; and 4,806,311. Therefore, in various embodiments, one or more analyte is detected from a sample obtained from a subject.

Samples

A sample is any material to be tested for the presence and/or concentration of an analyte. In general, a biological sample can be any sample taken from a subject, e.g., non-human animal or human and utilized in the test devices. For example, a biological sample can be a sample of any body fluid, cells, or tissue samples from a biopsy. Body fluid samples can include without any limitation blood, urine, sputum, semen, feces, saliva, bile, cerebral fluid, nasal swab, urogenital swab, nasal aspirate, spinal fluid, etc. Biological samples can also include any sample derived from a sample taken directly from a subject, e.g., human. For example, a biological sample can be the plasma fraction of a blood sample, serum, protein or nucleic acid extraction of the collected cells or tissues or from a specimen that has been treated in a way to improve the detectability of the specimen, for example, a lysis buffer containing a mucolytic agent that breaks down the mucens in a nasal specimen significantly reducing the viscosity of the specimen and a detergent to lyse the virus thereby releasing antigens and making them available for detection by the assay. A sample can be from any subject animal, including but not limited to, human, bird, porcine, equine, bovine, murine, cat, dog or sheep.

For example, a sample can be derived from any source, such as a physiological fluid, including blood, serum, plasma, saliva or oral fluid, sputum, ocular lens fluid, nasal fluid, nasopharyngeal or nasal pharyngeal swab or aspirate, sweat, urine, milk, ascites fluid, mucous, synovial fluid, peritoneal fluid, transdermal exudates, pharyngeal exudates, bronchio-alveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings and meat extracts are also considered biological fluids. Pretreatment may involve preparing plasma from blood, diluting or treating viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte. The selection and pretreatment of biological, industrial, and environmental samples prior to testing is well known in the art and need not be described further.

Other fields of interest include the diagnosis of veterinary diseases, analysis of meat, poultry, fish for bacterial contamination, inspection of food plants, food grains, fruit, dairy products (processed or unprocessed), restaurants, hospitals and other public facilities, analysis of environmental samples including water for beach, ocean, lakes or swimming pool contamination. Analytes detected by these tests include viral and bacterial antigens as well as chemicals including, for example, lead, pesticides, hormones, drugs and their metabolites, hydrocarbons and all kinds of organic or inorganic compounds.

In one aspect of the invention a kit is provided for detection of one or more analytes comprising: a sample collection device comprising; a sample tube 10; a sample collection implement 13; a dropper cap 14; a compartment comprising an extraction buffer FIG. 7(A); and a test device 19, FIG. 7B comprising one or more addressable regions configured for detection of one or more different analytes.

In some embodiments, the SCD comprises an extraction buffer comprising from about 0.75 to about 1.125M of salt in a buffered solution. In one embodiment, a salt in buffered solution is about 0.75M, 1M, 1.1M or 1.125M. In further embodiments, the extraction buffer contains about 1.0% to about 1.5% saponin. In yet further embodiments, saponin is at a concentration of about 0.75%, 1.0%, 1.1%, 1.2%, 1.3%, 1.4%, 1.5%, 1.6%, 1.7%, 1.8%, 1.9% or 2.0%. In further embodiments, a zwitterionic agent (e.g., Zwittergent 3/12) is provided to enhance extract of one or more analyte. For example, a zwitterion agent is provided in an extraction buffer at about 0.1% to about 1.5%. In yet further embodiments, a Zwittergent agent is at a concentration of about 0.1%, 0.15%, 0.175%, 0.2%, 0.225%, 0.25%, 0.275%, 0.3%, 0.325%, 0.350%, 0.375%, 0.4%, 0.425%, 0.450%, 0.475%, 0.5%, 0.525%, 0.550%, 0.575%, 0.6%, 0.7%, 0.75%, 1.0%, 1.1%, 1.2%, 1.3%, 1.4%, 1.5%, 1.6%, 1.7%, 1.8%, 1.9% or 2.0%. Examples of zwitterionic agent include Zwittergent 3/12;

most amino acids at physiological pH, Used as buffering agents in Good's buffers: the amino-sulfonic acid based MES, MOPS, HEPES, PIPES or CAPS; the amino-carboxylic acid (amino acid) based glycine, its derivatives bicine and tricine, and alanine; CHAPSO; natural products like the alkaloids psilocybin and lysergic acid; betaines; Quinonoid zwitterions; drugs such as Fexofenadine (Allegra) and Cephaloridine; 2-(N Morpholino)ethanesulfonic acid, (3-[N-Morpholino])propanesulfonic acid, 2-[(2-Amino-2-oxoethyl)amino]ethanesulfonic acid, piperazine-N,N'-bis(2-ethanesulfonic acid), 3-(N-Morpholino)-2-hydroxypropanesulfonic acid, N,N-Bis(2-hydroxyethyl)-2-aminoethanesulfonic acid, 3-(N-Morpholino) propanesulfonic acid, N-(2-Hydroxyethyl) piperazine-N'-(2-ethanesulfonic acid), N-Tris(hydroxymethyl)methyl-2 aminoethanesulfonic acid, 3-[N,N-Bis(2-hydroxyethyl) amino]-2-hydroxypropanesulfonic acid, 3-[N-Tris(hydroxymethyl)methylamino)-2-hydroxypropanesulfonic acid, N-(2-hydroxyethyl)piperazine-N'-(2-hydroxypropanesulfonic acid), piperazine-N,N'-bis(2-hydroxypropanesulfonic acid), N-(2-Hydroxyethyl)piperazine-N'-(3-propanesulfonic acid), N-Tris (hydroxymethyl)methyl-3-aminopropanesulfonic acid, 3-[(1,1-Dimethyl-2-hydroxyethyl)amino]-2-hydroxypropanesulfonic, acid, 2-(N-Cyclohexylamino)ethanesulfonic acid, 3-(cyclohexylamino)-2-hydroxy-1-propanesulfonic acid, 2-Amino-2-methyl-1-propanol, 3-(cyclohexylamino)-1-propanesulfonic acid, or mixtures thereof.

For example, extraction agents of the invention enhance extraction of membrane antigens including but not limited to haemagglutinin. Haemagglutinins are membrane glycoproteins well known to be associated with sphingolipid/cholesterol-enriched membrane domains (i.e. rafts; Detergent-insoluble glycolipid-enriched complexes (DIGs); or detergent resistant membranes, (DRMs)). In one embodiment, the combination of a zwitterionic detergent (e.g., Zwittergent 3-12), with Saponin (containing 20-35% sapogenin) mediates a rapid solubilization of H1, H3 and H5 influenza haemagglutinins. The solubilization by these agents enhance assay sensitivity for the haemagglutinin antigens without interfering with the detection of the nucleoproteins from Influenza A or Influenza B in the same assay.

In one embodiment the extraction reagent (buffer) is contained in a bulb in the handle of a SCD and a mucolytic agent is placed in the distal end of the SCD in dried or lyophilized state in such a way that when it is exposed to the extraction reagent the mucolytic reagent will be released and will aid in extracting the sample found on a swab or in a liquid specimen.

In some aspects of the invention, one or more analytes detected include but are not limited to one or more virus or virus components, one or more bacteria or bacterial components, one or more cancer cell or cancer cell component, one or more analyte associated with a heart damage, disease or condition, one or more analyte associated with a brain damage, disease or condition. In some embodiments, the one or more virus or viral components detected, are influenza A and/or influenza B. In further embodiments, the influenza A includes subtypes of a formula HxNy, where x is 1 through 16, and y is 1 through 9, or any combination of xy thereof. In one embodiment, the influenza A is H5N1.

In one embodiment, the dropper cap 14 comprises a plurality of detection probes and plurality of capture probes. In further embodiments, the dropper can comprise additional reagents or buffers (e.g., mucolytic reagent, salts, detergents, etc.). As used herein, a "capture probe" refers to a binding agent linked to a capture moiety and a "detection probe" or "label probe" refers to a binding agent linked to a label, detectable moiety or signal producing moiety, wherein each of the capture probe and detection probe is capable of specifically binding to a target analyte. Furthermore, for clarity, a "capture moiety partner" in the context of the Test Device (described below) refers to a complement, cognate or partner molecule that specifically binds to a capture moiety comprised on a capture probe. In various embodiments, devices and methods of the invention are configured to detect 1, 2, 3, 4, 5, 6, 7, 8, 9 or 10 different target analytes.

In one aspect of the invention, devices, systems and methods of the invention are configured to detect one or more analytes at a sensitivity and/or specificity of about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In some embodiments, devices, systems and methods of the invention are configured to provide a limit of sensitivity and specificity for detection an analyte of at least about 97%.

In yet other embodiments, devices, systems and methods of the invention are configured to detect of one or more analyte present where detection is at a sensitivity of at about (in pg/mL) 0.010, 0.020, 0.030, 0.040, 0.050, 0.060, 0.070, 0.080, 0.090, 0.10, 0.20, 0.30, 0.40, 0.50, 0.60, 0.70, 0.80, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 60.0, 70.0, 80.0, 90.0, 100, 150, 200, 250, 300, 400 or 500 pg/ml. In one embodiment, the sensitivity is at least from about 0.010 to about 0.10 pg/mL. In one embodiment, the sensitivity is at least about 0.030 pg/mL.

In some embodiments, detection of one or more analyte is at a sensitivity of about 0.25, 0.50, 0.75, 1.0, 1.25, 1.5, 1.75, 2.0, 2.5, 3.0, 4.0, 4.5, 5.0, 6.0, 7.0, 8.0, 9.0, 10, 15, 20, 25, 30, 35, 40, 45, 50, 55, 60, 65, 70, 80, 90 or about 100 attamoles. In one embodiment, the sensitivity for detection of each of one or more analytes is least about 1.5 attamoles.

In some embodiments, devices, systems and methods of the invention are configured to provide a limit of sensitivity for detection of each of said different analyte as measured by tissue culture infectious dose 50 ($TCID_{50}$) is from about $TCID_{50}$ of 1, 5, 10, 15, 20, 25, 50, 75, 100, 125, 150, 175, 200, 225, 250, 275, 300, 325, 350, 375, 400, 450, 500, 550, 600, 650, 700, 750, 800, 850, 900, 950 or about 1000 per mL. In one embodiment, sensitivity for detection of an analyte is at about 10 to about 200 $TCID_{50}$ per mL of sample. In one embodiment, sensitivity is at about 10 $TCID_{50}$.

In another aspect of the invention a method is provided for assaying a sample to detect one or more analytes comprising: administering a sample to a sample collection device (SCD) comprising; at least pair of a detection probe and a capture probe, each of which is capable of specifically binding an analyte; and a buffer for extracting said analyte from said sample; administering a sample from said SCD to a test device (TD) configured to detect said one or more analytes, wherein said TD comprises; a aperture for receiving said SCD and where said TD does not comprise a mobilizable entity capable of specifically binding said one or more analyte; at least one immobilized capture moiety which is capable of specifically binding a component of said capture probe; and thereby assaying said sample to detect said one or more analytes.

In various embodiments, the method comprises contacting a sample with an extraction buffer contains a salt in a buffered solution in concentrations as disclosed herein. In further embodiments, an extraction buffer contains saponin in concentrations as disclosed herein (e.g., supra).

In further embodiments, one or more analytes detected are one or more virus or virus components, one or more bacteria or bacterial components, one or more cancer cell or cancer cell component, one or more analyte associated with a heart damage, disease or condition or one or more analyte associated with a brain damage, disease or condition.

In one embodiment, the one or more analytes detected comprise influenza A and/or influenza B or components thereof. In further embodiments, the influenza A includes subtypes of a formula HxNy, where x is 1 through 16, and y is 1 through 9, or any combination of xy thereof. In one embodiment, the influenza A includes H5N1.

In another aspect of the invention a system is provided comprising: a sample collection device comprising, one or more pairs of detection probe and capture probe, wherein said one or more pairs is configured to detect one or more different analyte, a sampling implement; a test device comprising one or more immobilized capture moieties which are capable of specifically binding to said one or more capture probe, with the proviso that said test device does not comprise a mobilizable binding agent which is capable of binding specifically to said one or more different analyte.

In further embodiments, the system comprises a buffer containing salt in a buffered solution at concentrations disclosed herein. In further embodiments, the buffer comprises saponin at concentrations provided herein. Reagents for extraction of sample can be comprised in a SCD of the invention or mixed with a sample to form a solution that is subsequently added to a SCD of the invention.

In various embodiments, the system is configured for detection of one or more analytes including but not limited to one or more virus or virus components, one or more bacteria or bacterial components, one or more cancer cell or cancer cell component, one or more analyte associated with a heart damage, disease or condition or one or more analyte associated with a brain damage, disease or condition.

In some embodiments, the system is configured to detect one or more analytes comprising influenza A and/or influenza B virus or components thereof. In further embodiments, the influenza A includes subtypes of a formula HxNy, where x is 1 through 16, and y is 1 through 9, or any combination of xy thereof. In one embodiment, the influenza A includes H5N1.

In various embodiments, the system is configured to provide detection of one or more analytes at sensitivity and specificity as disclosed herein. For example, in one embodiment, sensitivity and/or specificity is at least about 97%.

In another embodiment, a system of the invention is configured to provide detection of one or more analyte at a sensitivity of at least about 0.030 pg/ml. In another embodiment, the system is configured to provide a limit of sensitivity for detection of each of said different analyte of at least about 1.5 attamoles. In yet another embodiment, the system is configured to provide sensitivity of at least about 10 to about 200 $TCID_{50}$ per mL for detection of an analyte as measured by tissue culture infectious dose 50 ($TCID_{50}$). In one embodiment, sensitivity is at least about 10 $TCID_{50}$.

In another aspect of the invention a method is provided for detecting one or more analytes comprising, administering a sample to a test device, wherein a device is configured to detect each of said one or more peptide at a sensitivity of at least about 0.30 pg/ml or 1.7 attamoles ($10^{-18}$), and of at least about 97% relative to a non-target analyte. In a further embodiment, one or more analyte (e.g., polypeptide, peptide, nucleic acid) is detected, which is associated with a condition selected from a group consisting of a brain condition, damage or disease, a heart condition, damage or disease, a cancer or neoplastic condition or disease, a liver condition, damage or disease, a kidney condition, damage or disease, or a combination thereof. In some embodiments, the one or more analyte detected is BNP, NT-proBNP, proBNP, CNP, and ANP.

In another embodiment, a method is provided for detection at least two or more virus in a sample comprising, administering a sample to a system comprising a SCD and TD, wherein said system is configured to detect each of said two or more virus at a sensitivity of about and specificity of at least about 97%.

In one embodiment, a method is provided for detection of one or more analyte comprising BNP, NT-proBNP, proBNP, CNP, and ANP, wherein said method comprises administering a sample to a device configured to detect the one or more analyte at a sensitivity of from about 5 to 10 pg/mL.

In various embodiments, a SCD (e.g., FIG. 1, 10) comprises a sampling implement that provides a means to collect a sample 21 from a subject, wherein the sampling implement is in fluid communication to the upper chamber via a sampling implement holder. The sampling implement is disposed at the distal end of a shaft, which shaft can be solid, hollow or semi-permeable. In some embodiments, the sampling implement is a swab, a comb, a brush, a spatula, a rod, a foam, a flocculated substrate or a spun substrate. In other embodiments, a sample can be added to the SCD 10 where the sample is a stored or previously obtained sample (e.g., archived blood sample). Therefore, in one embodiment a SCD can also be utilized without the need for a sample collection implement 21.

In various embodiments, an SCD comprises one or more sealed upper chambers wherein the seal functions as a valve to control fluid communication between the upper chamber and lower chamber of an SCD. In some embodiments, the valve can be a break-away valve, a flapper valve, a twist, screw, rupturable, puncturable or breakable valve. In other embodiments, the upper chamber can contain one or more ampoules which prevent solutions contained therein to flow to the lower chamber, unless pressure is exerted to rupture, puncture or break the ampoule so as to release any contents therein.

One aspect of the invention is directed to a SCD comprising a sample reservoir upstream of a plunger implement, a plurality of sealable apertures for delivery of one or more solutions, a substrate for filtering one or more compounds from a sample administered to the sample reservoir and reagents that are capable of specifically binding at least one analyte in said sample.

In another aspect of the invention, a Test Device is provided for detection of one or more analytes, wherein the device comprises a lateral flow membrane in a body, a chamber upstream of the lateral flow membrane containing a fluid or solution, wherein a gap is disposed between said chamber and said lateral flow membrane thus precluding fluid communication between the chamber and the lateral flow membrane. In one embodiment, the pressure exerted on the chamber pushes close the gap thus forming fluid communication between the chamber and the lateral flow membrane. In one embodiment, an opening into which a distal end of an SCD fits, is disposed directly above a wicking pad that is disposed downstream of the gap, but upstream of the lateral flow membrane.

In one embodiment, the Test Device chamber comprises one or more subchambers containing the same or different solutions. In other embodiments, the chamber of subchambers comprise one or more ampoules or packets that are breakable, puncturable or rupturable. Thus, where pressure is exerted on such ampoules or packets the contents are controllably released. As described herein, a Test Device can comprise a gap means or not comprise a gap means for disrupting fluid communication from the chamber to the lateral flow membrane. A Test Device gap can be from zero to 3.0, 0.5, to 3.5, 1.0 to 2.5, 1.0 to 3.0, or 2.0 to 4.0 mm.

In some embodiments, a Test Device can comprise a body housing the lateral flow membrane, wherein the body provides one or a plurality of windows through which the lateral flow membrane is visible. In various embodiments described herein, a Test Device comprises a lateral flow membrane that comprises a wicking substrate and an absorbent substrate upstream or downstream of the test zones disposed on said lateral flow membrane. In some embodiments, a substrate for collecting a small volume of sample for archiving is provided in a SCD or Test Device. In one embodiment, the substrate providing such archiving means is a filter, membrane or paper that collects a small volume of sample and said substrate is subsequently removed from the device.

In various embodiments, an SCD and/or Test Device comprises one or more identical identifiable tags, which can be removed from one device and placed on another device.

In some embodiments, the Test Device is shaped to only fit (specialized adaptor shape) into the receiving port of a reader if the upstream chamber has been depressed thus indicating that wash buffer or chase buffer contained therein has been released through the lateral flow membrane. In such embodiments, the Test Device and Reader specialized adaptor provides a means to verify that chase buffer or solution in the upstream chamber of the Test Device has been released and thus washed any sample present upstream of the lateral flow membrane through the lateral flow membrane. Thereby, the specialized adaptor provides a "safety means" to prevent reading of unprocessed samples.

In another aspect of the invention, the processed samples are run through the Test Device's lateral flow membrane, but can be placed aside from 30 minutes to several hours. In various embodiments, a plurality of samples can be run through the Test Device but read at 0.5, 1, 2, 3, 4, 5, 6, 7, 8, 9, 10, 11 or 12 hours later, with consistent and accurate signals.

In certain aspects of the invention, the devices disclosed herein are utilized in methods for detection of one or more analyte that may be present in a sample. In some embodiments, methods are directed to detecting one or more strain of an infectious agent. In one embodiment, a method is provided to detect one or more influenza virus and subtypes thereof. For example, methods are provided for detection of influenza virus A and B, and subtype of influenza A that may be present in a single sample.

In certain aspects of the invention a sample collection device (SCD) is provided for detection of one or more target antigens or analytes that may be present in a sample. The sample collection device can be utilized in conjunction with a test device (e.g., FIG. 1). In one aspect, a system is provided for detection of one or more analyte comprising a SCD, a Test Device and a Reader, as further described herein (e.g., FIG. 7).

In various embodiments, a SCD comprises one or more upper sealed chambers, which can contain the same or different solutions. In one embodiment, the upper sealed chamber comprises at least two compartments or subchambers each comprising the same or different reagents and/or buffers. In other embodiments, the upper chamber can comprise puncturable, breakable or rupturable ampoules. In some embodiments, a SCD provides the necessary reagents to form a complex with one or more different target antigens that may be present in a sample, wherein the complex comprises a capture moiety and a detectable label, a Test Device provides the necessary means to addressably capture one or more complexes so formed and a Reader which provides a means to detect one or more signals from addressably captured complexes.

In various embodiments, an upper sealed chamber comprising extraction buffer and/or reagents, a sample collection implement, a sample collection implement holder 10 and a plurality of reagents, wherein the reagents comprise a plurality of specific binding pairs, where each pair comprises a label 51 conjugated to first specific binding agent 52, 53 ("detection probe" or "label probe") and a capture moiety 56, 57 conjugated to a second specific binding agent 60 ("capture probe") where the first and second specific binding agents specifically bind a target antigen to form a complex. The capture moiety can be "captured" to a partner capture moiety 58, 59 immobilized on a substrate binds to the capture moiety-specific binding agent conjugate. In various embodiments, the specific binding agents are antibodies, thus a specific binding pair comprises an antibody-label conjugate ("label probe" or "detection probe") or antibody-capture moiety ("capture probe"). In such embodiments, a "partner capture moiety" is comprised on a test membrane disposed in a Test Device, which partner binds a specific capture probe, e.g., pRNA partner specifically binding a pRNA (i.e., capture moiety) contained on a capture probe (i.e., antibody specific for a target antigen).

In various embodiments, the plurality of specific binding agents comprise a multitude of groups of specific binding pairs, wherein each group comprises binding agents that specifically bind one target antigen, and a second group of binding pairs which specifically bind a second different antigen. Thus a plurality of specific binding pairs comprised in a SCD are capable of detecting a plurality of different target analytes.

In various embodiments, the capture moiety is an oligonucleotide, avidin, streptavidin, pyranosyl RNA (pRNA), aptamer, or a combination thereof. In various embodiments, the label is a metal, a fluorophore, a chromophore or a combination thereof. In some embodiments, the plurality of specific binding pairs comprised in a SCD can contain one type of capture moiety but with different capture moiety partners, e.g., each specific binding agent conjugated to pRNA, where each group that is specific to a different antigen comprises different pRNAs. In other embodiments, the plurality of specific binding pairs comprises one or more different capture moieties, e.g., pRNA for one group of specific binding pairs, while streptavidin for another, or a combination of different types of capture moieties.

In some embodiments, the plurality of specific binding pairs comprised in a SCD comprises one type of label (e.g., specific binding pairs where each group is conjugated to fluorophores having the same or fluorophores having different wavelength signals). In other embodiments, specific binding pairs comprise a combination of different types of labels (e.g., combination of metals and fluorophores). In one embodiment, the capture moiety is pRNA and the label is Europium.

In some embodiments, systems, devices and methods of the invention are configured to detect different analytes (i.e., target analytes; e.g., FIG. 5A, 55 and 54) which are from an infectious agent. Examples of infectious agents include but are not limited to yeast, fungus, bacteria, virus, and parasitic organisms. It should be understood that depending on the target analyte sought to be detected, an antibody or other specific binding agent is utilized (e.g., antibody, aptamer) which is specific for the particular target analyte. For example, antibodies can be raised to whatever the target analyte and incorporated into the systems, devices and methods of the invention.

In other embodiments, target analytes are infectious agents or components thereof, including but not limited to virus or viral components, bacteria or bacterial components, yeast or yeast components, fungus or fungal components, parasites or parasitic components, or any combination thereof.

In some embodiments, target analytes are virus or components of virus. In further embodiments, the different target analytes are from influenza virus and subtypes of influenza virus. For example, the influenza virus that can be detected is influenza virus A and B as well as subtypes of influenza virus. In one embodiment, an assay device is configured for detection of influenza virus strains A and B and subtypes of the formula HxNy, wherein x can be 1-16 and y can be 1-9, or any combination of xy thereof.

In one embodiment, a method is provided for determining whether a subject is infected with a pandemic, non-pandemic or strain of influenza virus for which vaccine is available.

In some embodiments, the Test Device excludes any reagent or binding agent that is capable of specifically binding a target analyte. In other words, the TD does not comprise an entity that specifically binds a target analyte.

In one aspect, a point of care ("POC") assay is provided based on lateral flow of fluid through nitrocellulose while employing techniques to reduce the background, improve the sensitivity and specificity of the assay. The detection technology employs a fluorescence detection system using a fluorophore. The fluorophore is coupled with a new capture system that enables the homogeneous binding of multiple monoclonal reagents to specific analytes and captures the complex onto specific test lines. More detail in this regard is provided in related U.S. application Ser. No. 11,677,559.

In one aspect of invention, an assay is provided which is capable of detecting one or more analytes at a sensitivity comparable to tissue culture infectious does 50 ($TCID_{50}$), where sensitivity is measurable at dilutions from about 1:100, about 1:1000, about 1:10,000, about 1:100,000 to about 1:1,000,000. In some embodiments, assays of the invention provide sensitivity measured from $TCID_{50}$ at about 0.003, 0.0035, 0.004, 0.0045, 0.005, 0.0055, 0.006, 0.0065, 0.007, 0.0075, 0.008, 0.0085, 0.009, 0.0095, 0.010, 0.0105, 0.020, 0.025, 0.030, 0.035, 0.040, 0.045, 0.050, 0.055, 0.060, 0.065, 0.070, 0.075, 0.080, 0.085, 0.090, 0.10, 0.20, 0.30, 0.40, 0.50, 0.60, 0.70, 0.80, 0.90, 1.0, 1.25, 1.50, 1.75, 2.0, 2.25, 2.5, 2.75, 3.0, 3.25, 3.5, 3.75, 4.0, 4.25, 4.5, 4.75, 5.0, 5.25, 5.50, 5.75, 6.0, 6.25, 6.50, 6.75, 7.0, 7.25, 7.5, 7.75, 8.0, 8.25, 8.5, 8.75, 9.0, 9.25, 9.5, 9.75 or about 10.0. In further embodiments, $TCID_{50}$ is from about 25, 50, 100, 125, 150, 175, 200, 225, 250, 275, 300, 325, 350, 375, 400, 425, 450, 475, 500, 525, 550, 575, to about 600 per mL.

In one embodiment, Type A and Type B analytes show at least two logs improvement in analyte sensitivity over a prior art POC Influenza assay.

In another aspect of the invention, the interface with the end user has been redeveloped resulting in a fully integrated sample collection device (SCD). These improvements enable high sensitivity multianalyte detection of a broad spectrum of analytes. In one embodiment, a single diagnostic assay simultaneously and separately detects the major subtypes of Influenza Type A and Type B, but also seasonal subtypes (I-IINI and H3N2), and pandemic subtype H5N1. This will provide the clinician and public health agency important real time or near real time information on influenza infection rates.

In one embodiment, for ease of use in a POC setting, a reader has been designed and has incorporated a simple to use icon driven interface. This will ensure that assays are recorded and frees personnel from the task of assay interpretation. This third generation POC assay is intended to simplify POC testing while moving towards more reliable results. Additional embodiments are disclosed in related U.S. patent application Ser. No. 11/677,559.

Sample Collection Device (SCD)

In one aspect of the invention a SCD is utilized to process a sample to allow detection of one or more analytes. For example, a SCD can incorporate a solid reagent component (e.g., capture and detection probes). Solid reagent components include, a powder, pill, bead, lyophilized pellet, pressed lyophilized power, dried on solid support (e.g., glass/plastic bead), lyophilized on or in association with a solid support or dried directly in the mixing or lower chamber. Such reagents are known in the art such as disclosed in CURRENT PROTOCOLS IN IMMUNOLOGY (Coligan, John E. et. al., eds. 1999).

In one embodiment of the invention, an SCD contains the following: A set of specimen extraction reagents in two separate reservoirs within the "handle" of the sample collection device. A lyophilized single use reagent or conjugate bead containing both capture and detection reagents. The capture MAb(s) for each analyte are conjugated to sequence specific pRNA capture molecules and detection MAb(s) which are conjugated to fluorescent microbeads.

In one embodiment an SCD comprises three components: (1) A set of swabs for collecting a nasopharyngeal, nasal or throat specimen; (2) A handle with extraction reagents containing with a valve mechanism (e.g., snap valve or puncturable seal) to release the reagents at the appropriate step in the assay; and (3) A plastic tube to contain the swab and the lyophilized reagent bead and a dropper tip (covered by a cap) to enable direct connection of the SCD to the Test Device (TD).

In another embodiment, the distal end of the SCD is open, whereby prior to release of a solution from the upper sealed chamber, the SCD is engaged (e.g., by friction fit) into the receiving port of a Test Device. In such an embodiment, the fluid flow from the distal end of the SCD into the Test Device is not regulated by a luer or a valve structure.

In another embodiment, the distal end of the SCD does not utilize a valve but rather is open. The SCD may be attached to the test device prior to release of the buffer from the upper chamber. Upon release of the solution from the upper chamber, the sample is released and/or extracted from the collection implement by the solution and mixed with the reagents located in the lower chamber. The mixture then flows to the test device for analysis of the presence of one or more analytes. It is possible to include water-dissolvable membranes within the lower chamber to slow the flow of the mixture out of the SCD onto the test device. Such membranes are conventional and can be designed to permit the retention of the mixture for differing periods of time sufficient to allow mixing and reaction of the reagents and sample analytes. For example, such membranes can be prepared from proteins, polysaccharides or film formers.

In another embodiment, the distal end of an SCD comprises a very narrow opening that prevents fluid flow unless and until pressure is applied to the device (e.g., via the bulb structure of the SCD, or if the housing is depressible, then by exerting pressure on the housing itself) to force the fluid out from the distal end. In other words, there is no valve of any sort disposed at the distal end of the SCD In some embodiments, the upper portion of the plastic tube has affixed a label flag that incorporates two removable barcodes, one that must be placed on the test device and one that may be place on the patient record. Additional embodiments are disclosed in related U.S. patent application Ser. No. 11,677,559.

In one embodiment, as shown in FIG. 1, the SCD contains the following: a sample tube 10 with a cap 23, an ampoule 11 containing liquid with antiseptic agent 12, such as sodium azide, a sampling implement 13 and a dropper cap 14. The conical tube may contain liquid 22 helpful for extraction of biological sample. In further embodiments, the dropper cap fits on the sample tube. The dropper cap is configured with an outlet 17 and a cap stopper 18 through which the content of the sample tube can be dispensed into sample receiving portion of Test Device 19. In further embodiments, lyophilized immunoreagents are added to the extraction mixture 22, or can be provided in a reagent chamber proximal to the open end of the SCD 10 or can be provided in the dropper cap 14. In one embodiment, the dropper cap contains lyophilized reagent inside of the dropper cap 14 (e.g., capture and detection probes to one or more different target analytes, 15, 16). In a further embodiment a screen (e.g., mesh or filter paper) is positioned 20 in the dropper cap. For example, the lyophilized reagents are held inside the dropper cap by a screen mesh 20, and/or the screen can function as a size-based or affinity-based filter of the extraction mixture 22.

In one embodiment, the SCD is configured with an compartment (e.g., ampoule or releasable compartment) 11 containing reagents (e.g., extraction buffer, and/or capture and detection probes). For example, during sample collection, the content of the compartment 11 can be dispensed into the sample tube 10. Furthermore, a sampling implement 21 (e.g., swab, cotton tip, needle) is used to obtain a cell, tissue, bodily fluid or other sample. The sampling implement is subject to the contents of the compartment 11 which contents can be released by the operator of the device.

In one embodiment, the sample tube is capped with the dropper cap 14 and inverted to provide filtering via the membrane 20 and/or to allow mixing with additional reagents 15, 16 provided in the dropper cap 14. A sample is dispensed through outlet port 17 into a Test Device 19.

Reagents utilized in an SCD of the invention can include one or more salts, chelators, anticoagulants, detergents, stabilizers, diluents, buffering agents, enzymes, cofactors, specific binding members, labels, mucolytic and the like. The one or more reagents can be compounds that facilitate analysis of a sample. Furthermore, such reagents can readily be adapted for use in a Test Device of the invention. In various embodiments, such reagents can be added to the sample tube 10 by the operator or can be contained in compartment 11 which is configured to form a screw type or friction fit with the sample tube 10 before release of the compartment 11 contents. Alternatively, reagents 22 can be present in the sample tube 10 with a puncturable seal, so that a sample implement can be used to subject the contents 22 to contact with the sample present on the sampling implement 22.

In one embodiment, an extraction buffer includes, (1.5× buffer): 0.075M Tris-Cl pH 8.5, 1.125M NaCl, 1.5% bovine serum albumin, 0.75% digested casein, 1.5% saponin, 0.375% zwittergent 3/12, 50 ug/ml gentamicin sulfate, 0.095% sodium azide, 0.025 mg/ml mouse IgG, 0.004% FD&C blue 1, 0.015% silicone antifoam. An extraction buffer provides enhanced extraction of a target analyte(s) (e.g., proteins or peptides from an infectious agent). In further embodiments, a composition of extraction buffer is comprised of a pH balancing agent, such as Tris-Cl, and other agents helpful for complete extraction of target moiety from the analytes, such as salt, serum, detergent, antibiotics, protein substrate such as casein and antiseptic agent. In yet other embodiments, an extraction buffer comprises a salt in a range from 0.5M to 1.5M, including but not limited to 0.5M NaCl, 0.6M NaCl, 0.7M NaCl, 0.8M NaCl, 0.9M NaCl, 1.0M NaCl, 1.1M, 1.2M, 1.3M, 1.4M, 1.5M; or from 0.8M to 1.5M, including but not limited to 0.85M NaCl, 0.95M NaCl, 1.05M NaCl, 1.1M NaCl, 1.2M NaCl, 1.3M NaCl, 1.4M NaCl, and 1.5M NaCl.

In other embodiments, extraction buffer further comprise saponin, in an amount ranging from 0.25% to 1.5%, including but not limited to about 0.25%, 0.3%, 0.4%, 0.5%, 0.6%, 0.7%, 0.8%, 0.9%, 1.0%, 1.25%, 1.3%, 1.4%, 1.5%, or from 0.03% to 0.08%, such as 0.0375%, 0.045%, 0.0475%, 0.05%, 0.055%, 0.0575%, 0.06%, 0.065%, 0.0675%, 0.07%, 0.075%, 0.08%. In one embodiment, saponin is from about 1% to 2%, including but not limited to about 1.1%, 1.2%, 1.3%, 1.4%, 1.5%, 1.6%, 1.7%, 1.8%, 1.9% to about 2.0%.

Test Device (TD)

Figure 2:
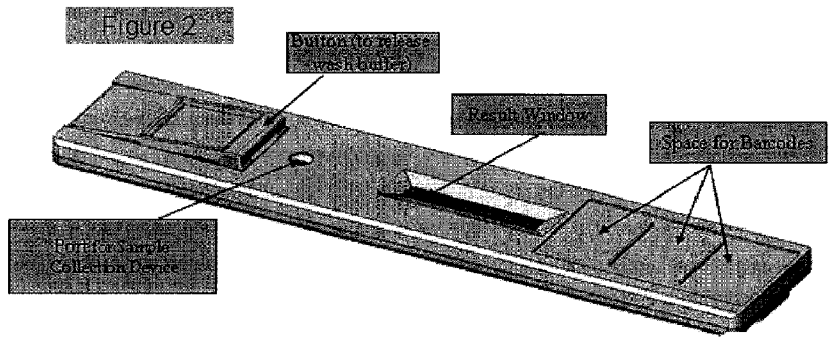
FIG. 2 illustrates a test device ("TD") designed for ease of use, barcode compatible and reducing/eliminating the potential of forming an aerosol of the specimen by having the Sample Collection Device ("SCD") attach directly to the TD.

As used herein in the context of the Test Device (e.g., FIG. 1, 19; FIG. 2) the terms "axial flow membrane", "lateral flow membrane", "test membrane", "test strip" or "matrix" are used interchangeably which employs capillary action to move or transport the test fluids or employs the movement of fluid separate from capillary action as where fluid is pumped by the accumulation of gas pressure, hydraulic pressure (direct pumping using a piston or rotary, bellows or other type pump on the assay fluids, electrostatic movement due to an electric field, gravity, etc.).

Another aspect of the invention is directed to a TD (FIG. 2) comprising a plastic housing with a port to which the SCD is easily affixed, a window for the reader to scan the rest result, and a button that the operator depresses after removing the SCD. In one embodiment a TD comprises: (I) A lateral flow test strip with a wicking membrane to adsorb the extracted specimen/reagent mixture; (2) A nitrocellulose strip with multiple lines. Each test line on the nitrocellulose test strip is striped with a unique pRNA (e.g., FIG. 5A: 56, 57, 58, 59), which captures its homologous binding pair with the specific capture agent (e.g., antibody) 60 attached; (3) An adsorbent pad 50 provides support the flow of fluid across the membrane; alternatively, the Test Device FIG. 2 comprises a (4) A buffer packet that is ruptured upon depressing the button allowing wash buffer to follow the specimen across the nitrocellulose pad aiding in the reduction of background and stopping the assay. Additional embodiments are disclosed in related U.S. patent application Ser. No. 11,677,559.

In one aspect, the signal obtained by the reader is processed using data processing software employing data reduction and curve fitting algorithms, optionally in combination with a trained neural network, to give either a positive or negative result for each test line, or a quantitative determination of the concentration of each analyte in the sample, which is correlated with a result indicative of a risk or presence of a disease or disorder. This result can optionally be input into a decision support system, and processed to provide an enhanced assessment of the risk of a medical condition as output. In one embodiment, the entire procedure may be automated and/or computer-controlled.

In one embodiment, the liquid transport along the test strip is based upon capillary action. In a further embodiment, the liquid transport along the matrix is based on non-bibulous lateral flow, wherein all of the dissolved or dispersed components of the liquid sample are carried at substantially equal rates and with relatively unimpaired flow laterally through the matrix, as opposed to preferential retention of one or more components as would occur, e.g., in materials that interact, chemically, physically, ionically or otherwise with one or more components. See for example, U.S. Pat. No. 4,943,522, hereby incorporated by reference in its entirety.

Any suitable material can be used to make the devices disclosed herein, such material including a rigid or semirigid, non-water-permeable material, such as glass, ceramics, metals, plastics, polymers, or copolymers, or any combination thereof. In some embodiments, either the SCD or Test Device comprise a plastic, polymer or copolymer such as those that are resistant to breakage, such as polypropylene, polyallomer, polycarbonate or cycloolefins or cycloolefin copolymers. Furthermore, devices of the invention can be made by appropriate manufacturing methods, such as, but not limited to, injection molding, blow molding, machining or press molding.

As used herein, test strip substrate refers to the material to which a capture moiety is linked using conventional methods in the art. A variety of materials can be used as the substrate, including any material that can act as a support for attachment of the molecules of interest. Such materials are known to those of skill in this art and include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone (PVP), rayon, nylon, polyethylene, polypropylene, polybutlyene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamide, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, or other commercially available media or a complex material composed of a solid or semi-solid substrate coated with materials that improve the hydrophilic property of the strip substrate, for example, polystyrene, Mylar, polyethylene, polycarbonate, polypropylene, polybutlyene, metals such as aluminum, copper, tin or mixtures of metals coated with dextran, detergents, salts, PVP and/or treated with electrostatic or plasma discharge to add charge to the surface thus imparting a hydrophilic property to the surface.

In one embodiment, the lateral flow membrane is comprised of a porous material such as high density polyethylene sheet material manufactured by Porex Technologies Corp. of Fairburn, Ga., USA. The sheet material has an open pore structure with a typical density, at 40% void volume, of 0.57 gm/cc and an average pore diameter of 1 to 250 micrometers, the average generally being from 3 to 100 micrometers. In another embodiment, the label zone is comprised of a porous material such as a nonwoven spunlaced acrylic fiber (similar to the sample receiving zone), e.g., New Merge or HDK material. Often, the porous material may be backed by, or laminated upon, a generally water impervious layer, e.g., Mylar. When employed, the backing is generally fastened to the matrix by an adhesive (e.g., 3M 444 double-sided adhesive tape). Typically, a water impervious backing is used for membranes of low thickness. A wide variety of polymers may be used provided that they do not bind nonspecifically to the assay components and do not interfere with flow of the fluid sample. Illustrative polymers include polyethylene, polypropylene, polystyrene and the like. On occasion, the matrix may be self-supporting. Other membranes amenable to non-bibulous flow, such as polyvinyl chloride, polyvinyl acetate, copolymers of vinyl acetate and vinyl chloride, polyamide, polycarbonate, polystyrene, and the like, can also be used. In yet another embodiment, the lateral flow membrane is comprised of a material such as untreated paper, cellulose blends, nitrocellulose, polyester, an acrylonitrile copolymer, and the like. The label zone may be constructed to provide either bibulous or non-bibulous flow, frequently the flow type is similar or identical to that provided in at least a portion of the sample receiving zone. In a frequent embodiment, the label zone is comprised of a nonwoven fabric such as Rayon or glass fiber. Other label zone materials suitable for use by the present invention include those chromatographic materials disclosed in U.S. Pat. No. 5,075,078, which is herein incorporated by reference.

In a frequent embodiment, the test strip substrate is treated with a solution that includes material-blocking and label-stabilizing agents. Blocking agents include bovine serum albumin (BSA), methylated BSA, casein, acid or base hydrolyzed casein, nonfat dry milk, fish gelatin, or similar. Stabilizing agents are readily available and well known in the art, and may be used, for example, to stabilize labeled reagents. In some embodiments, the upstream compartment containing a solution can comprise multiple ampoules, which can be selectively punctured or broken to release their contents. Therefore, in one embodiment, blocking reagents are contained in one ampoule which is utilized to pre-treat (e.g., "block") the test strip (i.e., lateral flow membrane), while the additional ampoule is reserved for washing the sample through the test strip.

The signal obtained by the reader is processed using data processing software employing data reduction and curve fitting algorithms, optionally in combination with a trained neural network, to give either a positive or negative result for each test line, or a quantitative determination of the concentration of each analyte in the sample, which is correlated with a result indicative of a risk or presence of a disease or disorder. This result can optionally be input into a decision support system, and processed to provide an enhanced assessment of the risk of a medical condition as output. In one embodiment, the entire procedure may be automated and/or computer-controlled.

As used herein, test strip substrate refers to the material to which a capture moiety is linked using conventional methods in the art. A variety of materials can be used as the substrate, including any material that can act as a support for attachment of the molecules of interest. Such materials are known to those of skill in this art and include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone (PVP), rayon, nylon, polyethylene, polypropylene, polybutlyene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamide, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, or other commercially available media or a complex material composed of a solid or semi-solid substrate coated with materials that improve the hydrophilic property of the strip substrate, for example, polystyrene, Mylar, polyethylene, polycarbonate, polypropylene, polybutlyene, metals such as aluminum, copper, tin or mixtures of metals coated with dextran, detergents, salts, PVP and/or treated with electrostatic or plasma discharge to add charge to the surface thus imparting a hydrophilic property to the surface.

In one embodiment, a test strip substrate is treated with a solution that includes material-blocking and label-stabilizing agents. Blocking agents include bovine serum albumin (BSA), methylated BSA, casein, acid or base hydrolyzed casein, nonfat dry milk, fish gelatin, or similar. Stabilizing agents are readily available and well known in the art, and may be used, for example, to stabilize labeled reagents. In some embodiments, the upstream compartment containing a solution can comprise multiple ampules, which can be selectively punctured or broken to release their contents. Therefore, in one embodiment, blocking reagents are contained in one ampule which is utilized to pre-treat (e.g., "block") the test strip (i.e., lateral flow membrane), while the additional ampule is reserved for washing the sample through the test strip.

The signal obtained by the reader is processed using data processing software employing data reduction and curve fitting algorithms, optionally in combination with a trained neural network, to give either a positive or negative result for each test line, or a quantitative determination of the concentration of each analyte in the sample, which is correlated with a result indicative of a risk or presence of a disease or disorder. This result can optionally be input into a decision support system, and processed to provide an enhanced assessment of the risk of a medical condition as output. In one embodiment, the entire procedure may be automated and/or computer-controlled.

In a frequent embodiment, the test strip substrate is treated with a solution that includes material-blocking and label-stabilizing agents. Blocking agents include bovine serum albumin (BSA), methylated BSA, casein, acid or base hydrolyzed casein, nonfat dry milk, fish gelatin, or similar. Stabilizing agents are readily available and well known in the art, and may be used, for example, to stabilize labeled reagents. In some embodiments, the upstream compartment containing a solution can comprise multiple ampules, which can be selectively punctured or broken to release their contents. Therefore, in one embodiment, blocking reagents are contained in one ampule which is utilized to pre-treat (e.g., "block") the test strip (i.e., lateral flow membrane), while the additional ampule is reserved for washing the sample through the test strip.

Exemplary functions of the labeled control reagents and zones include, for example, the confirmation that the liquid flow of the sample effectively solubilized and mobilized the labeled reagents from the SCD, which are captured in one or more defined test zones. Furthermore, controls can confirm that a sufficient amount of liquid traveled correctly through the test strip test and control zones, such that a sufficient amount of capture moieties could react with the corresponding specific capture probes complexed to a specific analyte (i.e., via the antigen specific binding agent). Further, control reagents confirm that the immunocomplexes (e.g., analyte-analyte specific binding agent) migrate onto the test region comprising the test and control zones, cross the test zone(s) in an amount such that the accumulation of the labeled analyte would produce a visible or otherwise readable signal in the case of a positive test result in the test zone(s). Moreover, an additional function of the control zones may be to act as reference zones which allow the user to identify the test results which are displayed as readable zones.

Since the devices of the present invention may incorporate one or more control zones, the labeled control reagent and their corresponding control zones are preferably developed such that each control zone will become visible with a desired intensity for all control zones after fluid sample is contacted with the device, regardless of the presence or absence of one or more analytes of interest.

In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control zones are present. Accordingly, the amount of capture reagent specific for the control label can be deposited in an amount that allows for the generation of desired signal intensity in the one or more control zones, and allows each of the control zones to restrain a desired amount of labeled control-reagent. At the completion of an assay, each of the control zones preferably provide a desired and/or pre-designed signal (in intensity and form). Examples of contemplated pre-designed signals include signals of equal intensities in each control zone, or following a desired pattern of increasing, decreasing or other signal intensity in the control zones.

In another embodiment, each control zone will be specific for a unique control reagent. In this embodiment, the label zone may include multiple and different labeled control reagents, equaling the number of control zones in the assay, or a related variation. Wherein each of the labeled control reagents may become restrained in one or more pre-determined and specific control zone(s). These labeled control reagents can provide the same detectable signal (e.g., be of the same color) or provide distinguishable detectable signals (e.g., have different colored labels or other detection systems) upon accumulation in the control zone(s).

In yet another embodiment, the control zones may include a combination of the two types of control zones described in the two previous embodiments, specifically, one or more control zones are able to restrain or bind a single type of labeled control reagent, and other control zones on the same test strip will be capable of binding one or several other specifically labeled control reagents.

In one embodiment, the labeled control reagent comprises a detectable moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control zone. Thus the labeled control reagent is directly restrained in the control zone.

In another embodiment, the detectable moiety which forms the label component of the labeled control reagent is the same detectable moiety as that which is utilized as the label component of the analyte of interest labeled test reagent. In a frequent embodiment, the label component of the labeled control reagent is different from the label component of the labeled test reagent, so that results of the assay are easily determined. In another frequent embodiment, the control label and the test label include colored beads, e.g., colored latex. Also frequently, the control and test latex beads comprise different colors.

In a further embodiment, the labeled control reagent includes streptavidin, avidin or biotin and the control capture partner includes the corresponding member of such specific binding pairs, which readily and specifically bind with one another. In one example, the labeled control reagent includes biotin, and the control capture partner includes streptavidin.

The artisan will appreciate that other members of specific binding pairs can alternatively be used, including, for example, antigen/antibody reactions unrelated to analyte. In yet other embodiment, capture partners can include any of the binding moieties disclosed herein.

The use of a control zone is helpful in that appearance of a signal in the control zone indicates the time at which the test result can be read, even for a negative result. Thus, when the expected signal appears in the control line, the presence or absence of a signal in a test zone can be noted.

In still further embodiment, a control zone comprising a mark that becomes visible in the test region when the test region is in a moist state is utilized. Control zones of this type are described in U.S. patent application Ser. No. 09/950,366, filed, Sep. 10, 2001, currently pending and published as U.S. patent application Publication No. 20030049167, and Ser. No. 10/241,822, filed Sep. 10, 2002, currently pending and published as U.S. patent application Publication No. 20030157699.

In some embodiments, one or more control zones of this type are utilized. In another embodiment, a combination of control zones of the type utilizing labeled control reagents and control zone and of the type that display the control zone when in a moist state can be used. This allows a simple way to formulate control zones while allowing to use a reagent-based control zone to ascertain that the re-solubilization and mobilization of the reagents in SCD-processed samples has been effective, and that the specific reactions took place as expected, all along the path defined Test Device, wick, test strip and absorbent pad. The present embodiment includes the use of one or more control zones that become visible when the test region is in the moist state for each of the control zones of an assay, except the control zone on the distal or downstream end of the test strip.

The present description further provides means to build a rapid, multi-analyte assay, which is needed in many fields of environmental monitoring, medicine, particularly in the field of infectious disease. For example, contemplated devices include those useful for the differential diagnosis of Flu A or Flu B, and subtypes thereof (e.g., Flu A, H5N1) which may result in different treatments, or the differential diagnosis of Flu A, Flu B, and/or RSV in one step. Such devices permit the use of a single sample for assaying multiple analytes at once, and beneficially allows for a considerable reduction of the hands-on time and duration of the diagnostic process for the benefit of the doctor, or user in general. As such a plurality of immunoreagents can be utilized in an SCD of the invention, where said plurality comprises populations of specific binding agents, comprising pairs conjugated respectively to label and capture moiety, whereby said plurality comprise multiple populations each specific for a different analyte as compared to any other population. For example, the plurality of immunoreagents can be specific for several types of one pathogen or different pathogens.

A variety of analytes may be assayed utilizing devices and methods of the present disclosure. In a particular device useful for assaying for one or more analytes of interest in a sample, the collection of analytes of interest may be referred to as a panel. For example, a panel may comprise any combination (or all of) of influenza A, influenza B, influenza A subtypes, respiratory syncytial virus (RSV), adenovirus, and different types of Parainfluenza viruses (for example Types 1, 2, 3 etc.). Another panel may comprise testing for a selection of one or more of upper respiratory infection including, for example, *Streptococcus pneumoniae, Mycoplasma pneumoniae* and/or *Chlamydia pneumoniae*. Yet another panel can be devised for the diagnosis of sexually transmitted disease including, for example, *Chlamydia, Trichomonas* and/or *Gonorrhea*. In each case, a particular panel devised to provide signals on the Test Device for a particular series of analytes is readily obtained by incorporating a different set of detection and capture probes in the SCD, which is described herein. Therefore, a particular SCD will provide all the reagents necessary to detect a particular panel of analytes which are detected when using a Test Device employing test strips that have detection reagents that are not specific for the analytes of interest. In other embodiments, a broad scope Test Device can comprise non-specific capture moieties for several series of analytes from related or distinct pathogens, e.g., detection of HIV and HCV antigens; HIV and tuberculosis, Influenza A, B, and subtypes of A, bacterial and viral infections. Thus a single Test Device can be used with SCDs comprising immunoreagents for a different panel of analytes, providing enhanced efficiency and cost effectiveness.

For example, a panel may optionally include a variety of other analytes of interest, including SARS-associated coronavirus, influenza A; a hepatitis panel comprising a selection of hepatitis B surface Ag or Ab, hepatitis B core Ab, hepatitis A virus Ab, and hepatitis C virus; a phospholipids panel comprising a selection of Anticardiolipin Abs (IgG, IgA, and IgM Isotypes); an arthritis panel comprising a selection of rheumatoid factor, antinuclear antibodies, and Uric Acid; an Epstein Barr panel comprising a selection of Epstein Barr Nuclear Ag, Epstein Barr Viral Capsid Ag, and Epstein Barr Virus, Early Antigen; other panels include HIV panels, Lupus panels, *H. Pylori* panels, toxoplasma panels, herpes panels, *Borrelia* panels, rubella panels, cytomegalovirus panels, panels testing for recent myocardial infarction with analytes comprising an isotype of Troponin with myoglobin and/or CKMB and many others. One of skill in the art would understand that a variety of panels may be assayed via the immunoassays utilizing the devices disclosed herein. Immunoassay methods are known in the art. See, e.g., CURRENT PROTOCOLS IN IMMUNOLOGY (Coligan, John E. et. al., eds. 1999).

Numerous analytical devices known to those of skill in the art may be adapted in accordance with the present invention, to detect multiple analytes. By way of example, dipstick, lateral flow and flow-through devices, particularly those that are immunoassays, may be modified in accordance herewith in order to detect and distinguish multiple analytes. Exemplary lateral flow devices include those described in U.S. Pat. Nos. 4,818,677, 4,943,522, 5,096,837 (RE 35,306), 5,096, 837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, 6,306,642. Other lateral flow devices that may be modified for use in distinguishable detection of multiple analytes in a fluid sample include U.S. Pat. Nos. 4,703,017, 6,187,598, 6,352, 862, 6,485,982, 6,534,320 and 6,767,714. Exemplary dipstick devices include those described in U.S. Pat. Nos. 4,235, 601, 5,559,041, 5,712,172 and 6,790,611. It will be appreciated by those of skill in the art that the aforementioned patents may and frequently do disclose more than one assay configuration and are likewise referred to herein for such additional disclosures. Advantageously, the improvements described are applicable to various assay, especially immunoassay, configurations.

Reader

Figure 3:
FIG. 3 illustrates an optical reader.

In yet a further aspect of the invention a reader provides effective detection. In one embodiment, an icon driven fluorescent reader (FIG. 3) is required to read the bar coded information on the TD, ensuring the components are in date and returns a result for each analyte line. Additional embodiments are disclosed in related U.S. patent application Ser. No. 11/677,559.

Multianalyte

In one aspect of the invention, one or more analytes are detected using methods, systems and devices of the invention. As disclosed herein, a sample can be from any source and the invention is configured to provide enhanced sensitivity and specificity for detecting an analyte, while providing capabilities to detect a plurality of different analytes. The type of analytes that can be detected are discussed herein.

Rapid influenza tests have been marketed for years. Most of these tests are lateral flow immunoassay tests using either gold or latex as the visualization agent. While most of new rapid immunoassays are able to differentiate influenza Type A from influenza Type B, only few of them have both test lines for type A and type B on the one strip. However, none of these tests are designed to differentiate subtypes of influenza type A. Therefore these tests may be able to detect avian influenza, none of them can tell if a patient is infected by a seasonal flu A virus or a more severe Type A subtype such as H5N1 termed avian influenza (or current potential pandemic subtype of influenza A). The present invention is designed on concepts that when applied are to yield a highly sensitive assay with improved reproducibility, able to detect type A, type B and differentiate subtype H5N1 from seasonal flu (subtypes H1 and H3) and is easy to use. Efforts have been made to apply multiple new technologies with a new device design, such as pre-mixing of the sample with the conjugate, use of a chasing or wash buffer to reduce background, employ a unique generic capture reagent pRNA which allows multiple analytes detection at high sensitivity, fluorescent label which is highly sensitive, etc. The combination of these approaches enables a novel and highly effective influenza rapid test that is much more sensitive, provides low cost production, ease of operate and has the ability to differentiate seasonal flu from pandemic avian flu H5N1.

In one embodiment, the combination of features described herein are responsible for the excellent sensitivity and reproducibility of assays constructed in accordance with the invention to use the novel system, which serves to concentrate ligand from a test sample at a test site the test strip, and the use of a metal sol or other colored particle as a marker system which penults persistent visual observation of the fluorescence over a period of one to several hours beyond the minimum time needed to complete the assay). Background noise is reduced while maintaining excellent sensitivity by including in the test implement a controllably released buffer that functions to wash away excess/unbound label. Furthermore, one or more control sites whose color is compared with the test site. In some embodiments, a filtration means is comprised in the sample implement or in the test implement, which filtration means limits the introduction to the test site of contaminants from the crude or unprocessed biological sample.

Assay Methods.

In one embodiment, an assay method comprises the steps of applying the sampling implement to a subject or subject's biological sample, to collect a sample (e.g., swabbing inside the nose, mouth, throat, ear; applying a sampling element to a biological sample obtained from a subject), inserting the collection implement into the sample collection device housing chamber, squeezing the upper chamber to break open the snap-valve and allowing a buffer to run down to the sampling implement, thus immersing the biological sample disposed thereon and running the mixture of buffer and sample into a reaction chamber (e.g., lower chamber) where a plurality of capture and detection probes bind to their specific target analyte. Subsequently or concurrently, the mixture is expelled from the distal end of the SCD into a Test Device comprising immobilized capture moieties designed to capture a complex of analyte and detection/capture probe, via the complementary capture moiety linked to a capture probe. Thus, a particular capture probe is designed to be complementary to an immobilized capture moiety for one particular analyte. Furthermore, as disclosed herein, capture moieties are disposed on a lateral flow membrane in distinct positions/patterns, where a single line or spot(s) if detected via the signal emitting label, allows qualitative and/or quantitative detection of a particular analyte. Therefore, by patterning particular capture probes on the lateral flow membrane, an assay method can detect a panel of the same or related infectious agent or even unrelated infectious agents, as disclosed herein.

In some embodiments a sandwich immunoassay format is utilized but any conventional format, including a competitive assay, may be used. Typically, an indirect capture of the formed immunocomplex is utilized in the sandwich format. One or more analytes in the sample are contacted with one or more pairs of a detection probe and a capture probe. Each pair contains the detection probe which is a conjugate comprising a label and a specific binding agent (SBA) capable of specifically binding to an analyte and a capture probe which is a conjugate comprising a detection moiety and another SBA capable of specifically binding the same analyte. Examples of specific binding agent(s) include antibodies, aptamers, In one embodiment, each of two SBAs are specific binding partners in that each bind the same target antigen or analyte.

Examples of SBAs are known in the art and include but are not limited to antibodies, aptamers or oligonucleotides. In the sandwich assay, the analyte is simultaneously bound by both the detection probe and the capture probe. The detection moiety is part of a specific binding pair and the other partner of the pair is immobilized on the test device to capture the immunocomplex as it flows through the test device. The use of different capture moiety pairs for each different analyte permits the detection of multiple analyte on one test device from a single sample and reaction sequence. In most cases, the labels for each analyte are different. However, by having a specific location for each analyte as a capture zone with distinct capture moiety pairs for each analyte, it is possible to utilize the same label for all of the analyte.

Binding Reagents

One aspect of the invention is directed to binding reagents disposed in the SCD. For example, in some immunoassays, an antibody pair is utilized, where each member of the pair can specifically bind the same target analyte, wherein one antibody is a capture antibody and the other is a detection antibody. A capture antibody is linked, directly or indirectly, to a capture moiety which is "captured" by a cognate immobilized capture moiety disposed on a solid support (e.g., nitrocellulose membrane). Furthermore, the detection antibody (i.e., detection probe) is linked to a detectable label. The detection antibody is preferably labeled by conjugation to a physically detectable label, and upon contacting with the sample containing the target analyte forms a complex. The antibody-analyte complex can then be immobilized on a solid support via the capture moiety. The resulting complex immobilized on the solid support, is detectable by virtue of the label.

In one embodiment, the SCD reagent solution or solid substrate comprises a plurality of different detection probes, each detection probe capable of binding to a different target and each detection probe being labeled with or enabling the formation of a detection signal so that the presence of each target is indicated by the formation of a signal at the test zone for that target (i.e., in the Test Device); wherein the target for at least two of the capture moieties is an infectious agent or a disease causing micro-organism or a marker indicating the existence of a disease, disorder, or condition of the host from which the sample solution was derived, and wherein at least two of the capture moieties are capable of binding to different components or markers of the same infectious agent or disease causing microorganism, or to different markers for the same disease, disorder, or condition not caused by an infectious agent or disease causing microorganism, as targets for those capture moieties. Furthermore, the SCD will also comprise a plurality of different capture probes, each of which is paired up with a detection probe, where the pairing is defined by the capability to bind a particular target analyte.

As used herein, the term "specifically binds" refers to the binding specificity of a specific binding pair. "Specific binding pair member" refers to a member of a specific binding pair ("sbp"), which means two different molecules wherein one of the molecules specifically binds with the second molecule through chemical or physical means. For example, a pair of pRNAs or an aptamer/target antigen pair, or streptavidin-biotin provide exemplary specific binding pair members or sbp. The two molecules are related in the sense that their binding with each other is such that they are capable of distinguishing their binding partner from other assay constituents having similar characteristics. The members of the specific binding pair are referred to as ligand and receptor (antiligand), sbp member and sbp partner, and the like. A molecule may also be a sbp member for an aggregation of molecules; for example an antibody raised against an immune complex of a second antibody and its corresponding antigen may be considered to be a sbp member for the immune complex.

In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence or chemical moiety (such as digoxin/anti-digoxin) and an antibody specific for the sequence, chemical moiety or the entire protein, polymeric acids and bases, dyes and protein binders, peptides and specific protein binders (e.g., ribonuclease, S-peptide and ribonuclease S-protein), metals and their chelators, and the like. Furthermore, specific binding pairs can include members that are analogs of the original specific binding member, for example an analyte-analog or a specific binding member made by recombinant techniques or molecular engineering.

A sbp member is analogous to another sbp member if they are both capable of binding to another identical complementary sbp member. Such a sbp member may, for example, be either a ligand or a receptor that has been modified by the replacement of at least one hydrogen atom by a group to provide, for example, a labeled ligand or labeled receptor. The sbp members can be analogous to or complementary to the analyte or to an sbp member that is complementary to the analyte. If the specific binding member is an immunoreactant it can be, for example, an antibody, antigen, hapten, or complex thereof. If an antibody is used, it can be a monoclonal or polyclonal antibody, a recombinant protein or antibody, a chimeric antibody, a mixture(s) or fragment(s) thereof, as well as a mixture of an antibody and other specific binding members. Other examples of binding pairs that can be incorporated into the detection molecules are disclosed in U.S. Pat. Nos. 6,946,546, 6,967,250, 6,984,491, 7,022,492, 7,026,120, 7,022,529, 7,026,135, 7,033,781, 7,052,854, 7,052,916 and 7,056,679.

"Antibody" refers to a polypeptide substantially encoded by an immunoglobulin gene or immunoglobulin genes, or fragments thereof, and includes any immunoglobulin, including monoclonal antibodies, polyclonal antibodies, multispecific or bispecific antibodies, that bind to a specific antigen. A complete antibody comprises two heavy chains and two light chains. Each heavy chain consists of a variable region and a first, second, and third constant region, while each light chain consists of a variable region and a constant region. The antibody has a "Y" shape, with the stem of the Y consisting of the second and third constant regions of two heavy chains bound together via disulfide bonding. Each arm of the Y consists of the variable region and first constant region of a single heavy chain bound to the variable and constant regions of a single light chain. The variable regions of the light and heavy chains are responsible for antigen binding. The variable region in both chains generally contains three highly variable loops called the complementarity determining regions (CDRs) (light (L) chain CDRs including LCDR1, LCDR2, and LCDR3, heavy (H) chain CDRs including HCDR1, HCDR2, HCDR3) (as defined by Kabat, et al., Sequences of Proteins of Immunological Interest, Fifth Edition (1991), vols. 1-3, NIH Publication 91-3242, Bethesda Md.). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes and subclasses include IgG, IgG1, IgG2, IgG3, IgG4, IgM, IgA, IgA1, or IgA2, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods. The term "antibody" as used herein Antibodies are assigned to classes based on the amino acid sequence of the constant region of their heavy chain. The major classes of antibodies are IgA, IgD, IgE, IgG, and IgM, with several of these classes divided into subclasses such as.

In addition to an intact immunoglobulin, the term "antibody" as used herein further refers to an immunoglobulin fragment thereof (i.e., at least one immunologically active portion of an immunoglobulin molecule), such as a Fab, Fab', F(ab')$_2$, Fv fragment, a single-chain antibody molecule, a multispecific antibody formed from any fragment of an immunoglobulin molecule comprising one or more CDRs. In addition, an antibody as used herein may comprise one or more CDRs from a particular human immunoglobulin grafted to a framework region from one or more different human immunoglobulins.

"Fab" with regards to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'.

"Fc" with regards to an antibody refers to that portion of the antibody consisting of the second and third constant regions of a first heavy chain bound to the second and third constant regions of a second heavy chain via disulfide bonding. The Fc portion of the antibody is responsible for various effector functions but does not function in antigen binding.

"Fv" with regards to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Houston 1988).

"Single-chain Fv-Fc antibody" or "scFv-Fc" refers to an engineered antibody consisting of a scFv connected to the Fc region of an antibody.

The term "epitope" as used herein refers to the group of atoms and/or amino acids on an antigen molecule to which an antibody binds.

The term "monoclonal antibody" as used herein refers to an antibody or a fragment thereof obtained from a population of substantially homogeneous antibodies, i.e., the individual antibodies comprising the population are identical except for possible naturally occurring mutations that may be present in minor amounts. Monoclonal antibodies are highly specific, being directed against a single epitope on the antigen. Monoclonal antibodies are in contrast to polyclonal antibodies which typically include different antibodies directed against different epitopes on the antigens. Although monoclonal antibodies are traditionally derived from hybridomas, the monoclonal antibodies of the present invention are not limited by their production method. For example, the monoclonal antibodies of the present invention may be made by the hybridoma method first described by Kohler et al., Nature, 256:495 (1975), or may be made by recombinant DNA methods (see, e.g., U.S. Pat. No. 4,816,567).

The term "chimeric antibody" as used herein refers to an antibody in which a portion of the heavy and/or light chain is identical with or homologous to corresponding sequences in antibodies derived from a particular species or belonging to a particular antibody class or subclass, while the remainder of the heavy and/or light chain is identical with or homologous to corresponding sequences in antibodies derived from another species or belonging to another antibody class or subclass, as well as fragments of such an antibody, so long as such fragments exhibit the desired antigen-binding activity (U.S. Pat. No. 4,816,567 to Cabilly et al.; Morrison et al., Proc. Natl. Acad. Sci. USA, 81:6851 6855 (1984)).

The term "humanized antibody" used herein refers to an antibody or fragments thereof which are human immunoglobulins (recipient antibody) in which residues from part or all of a CDR of the recipient are replaced by residues from a CDR of a non-human species (donor antibody) such as mouse, rat or rabbit having the desired specificity, affinity, and capacity. In some instances, FR residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin Fc region, typically that of a human immunoglobulin. For further details, see Jones et al., Nature, 321:522 525 (1986); Reichmann et al., Nature, 332:323 329 (1988); Presta, Curr. Op. Struct. Biol., 2:593 596 (1992); and Clark, Immunol. Today 21: 397 402 (2000).

In various embodiments, a device of the invention is configured for use with anti-H5 monoclonal antibodies that are produced by mice hybridoma cell strains as disclosed in U.S. application Ser. No. 11/677,559. Antibodies are designed to specifically bind to the hemagglutinin of subtype H5 avian influenza virus. For example, the mice hybridoma cell strains 8H5, 3C8, 10F7, 4D1, 3G4, and 2F2 were deposited in China Center for Typical Culture Collection (CCTCC, Wuhan University, Wuhan, China) on Jan. 17, 2006 with deposit numbers of CCTCC-C200607 (hybridoma cell strain 8H5), CCTCC-C200605 (hybridoma cell strain 3C8), CCTCC-C200608 (hybridoma cell strain 10F7), CCTCC-C200606 (hybridoma cell strain 4D1), CCTCC-C200604 (hybridoma cell strain 3G4) and CCTCC-C200424 (hybridoma cell strain 2F2).

The present invention also provides monoclonal antibodies that block the binding of monoclonal antibodies 8H5, 3C8, 10F7, 4D1, 3G4, or 2F2 to the hemagglutinin of subtype H5 avian influenza virus. Such blocking monoclonal antibodies may bind to the same epitopes on the hemagglutinin that are recognized by monoclonal antibodies 8H5, 3C8, 10F7, 4D1, 3G4, or 2F2. Alternatively, those blocking monoclonal antibodies may bind to epitopes that overlap sterically with the epitopes recognized by monoclonal antibodies 8H5, 3C8, 10F7, 4D1, 3G4, or 2F2. These blocking monoclonal antibodies can reduce the binding of monoclonal antibodies 8H5, 3C8, 10F7, 4D1, 3G4, or 2F2 to the hemagglutinin of subtype H5 avian influenza virus by at least about 50%. Alternatively, they may reduce binding by at least about 60%, preferably at least about 70%, more preferably at least about 75%, more preferably at least about 80%, more preferably at least about 85%, even more preferably at least about 90%, even more preferably at least about 95%, most preferably at least about 99%.

The ability of a test monoclonal antibody to reduce the binding of a known monoclonal antibody to the H5 hemagglutinin may be measured by a routine competition assay such as that described in *Antibodies: A Laboratory Manual*, Cold Spring Harbor Laboratory, Ed Harlow and David Lane (1988). For example, such an assay could be performed by pre-coating a microtiter plate with antigens, incubating the pre-coated plates with serial dilutions of the unlabeled test antibodies admixed with a selected concentration of the labeled known antibodies, washing the incubation mixture, and detecting and measuring the amount of the known antibodies bound to the plates at the various dilutions of the test antibodies. The stronger the test antibodies compete with the known antibodies for binding to the antigens, the more the binding of the known antibodies to the antigens would be reduced. Usually, the antigens are pre-coated on a 96-well plate, and the ability of unlabeled antibodies to block the binding of labeled antibodies is measured using radioactive or enzyme labels.

Monoclonal antibodies may be generated by the hybridoma method first described by Kohler et al., Nature, 256: 495 (1975). In the hybridoma method, a mouse or other appropriate host animal is immunized by one or more injections of an immunizing agent and, if desired, an adjuvant.

Typically, the immunizing agent and/or adjuvant will be injected in the host animal by multiple subcutaneous or intraperitoneal injections. It may be useful to conjugate the immunizing agent to a protein known to be immunogenic in the host animal being immunized, such as serum albumin, or soybean trypsin inhibitor. Examples of adjuvants which may be employed include Freund's complete adjuvant and MPL-TDM. After immunization, the host animal makes lymphocytes that produce or are capable of producing antibodies that will specifically bind to the antigen used for immunization. Alternatively, lymphocytes may be immunized in vitro. Desired lymphocytes are collected and fused with myeloma cells using a suitable fusing agent, such as polyethylene glycol, to form a hybridoma cell (Goding, *Monoclonal Antibodies: Principles and Practice*, pp. 59 103, Academic Press, 1996).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and MC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133: 3001 (1984); Brodeur et al., *Monoclonal Antibody Production Techniques and Applications*, pp. 51-63, Marcel Dekker, Inc., New York, 1987).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis of Munson et al., Anal. Biochem., 107: 220 (1980).

After hybridoma cells are identified that produce antibodies of the desired specificity, affinity, and/or activity, the cells may be subcloned by limiting dilution procedures and grown by standard methods (Goding, Monoclonal Antibodies: Principles and Practice, pp. 59-103, Academic Press, 1996). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies of the invention may also be made by conventional genetic engineering methods. DNA molecules encoding the heavy and light chains of the monoclonal antibodies may be isolated from the hybridoma cells, for example through PCR using oligonucleotide probes that are capable of binding specifically to genes encoding the heavy and light chains of the monoclonal antibodies. Then the DNA molecules are inserted into expression vectors. The expression vectors are transfected into host cells such as *E. coli* cells, simian COS cells, Chinese hamster ovary (CHO) cells, or myeloma cells that do not otherwise produce immunoglobulin protein. The host cells are cultured under conditions suitable for the expression of the antibodies.

The antibodies used bind to the H5 hemagglutinin with high specificity and affinity. The antibodies shall have low cross-reactivity with other subtypes of hemagglutinin, preferably no cross-reactivity with other subtypes of hemagglutinins. In one aspect, the invention provides antibodies that bind to H5 hemagglutinin with a $K_D$ value of less than $1\times10^{-5}$M. Preferably, the $K_D$ value is less than $1\times10^{-6}$M. More preferably, the $K_D$ value is less than $1\times10^{-7}$M. Most preferably, the $K_D$ value is less than $1\times10^{-8}$M.

The antibodies of the invention may contain the conventional "Y" shape structure comprised of two heavy chains and two light chains. In addition, the antibodies may also be the Fab fragment, the Fab' fragment, the $F(ab)_2$ fragment or the Fv fragment, or another partial piece of the conventional "Y" shaped structure that maintains binding affinity to the hemagglutinin. The binding affinity of the fragments to hemagglutinin may be higher or lower than that of the conventional "Y" shaped antibodies.

The antibody fragments may be generated via proteolytic digestion of intact antibodies (see, e.g., Morimoto et al., J. Biochem. Biophys. Methods, 24:107-117, (1992) and Brennan et al., Science, 229:81 (1985)). Additionally, these fragments can also be produced directly by recombinant host cells (reviewed in Hudson, Curr. Opin. Immunol, 11: 548-557 (1999); Little et al., Immunol. Today, 21: 364-370 (2000)). For example, Fab' fragments can be directly recovered from *E. coli* and chemically coupled to form $F(ab')_2$ fragments (Carter et al., Bio/Technology, 10:163 167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. Other techniques for the production of antibody fragments will be apparent to a person with ordinary skill in the art.

The present invention provides isolated nucleic acid molecules encoding antibodies or fragments thereof that specifically bind to H5 hemagglutinin. Nucleic acid molecules encoding the antibodies can be isolated from hybridoma cells. The nucleic acid sequences of the molecules can be determined using routine techniques known to a person with ordinary skill in the art. Nucleic acid molecules of the invention can also be prepared using conventional genetic engineering techniques as well as chemical synthesis. In one aspect, the present invention provides an isolated nucleic acid molecule encoding the variable region of the heavy chain of an anti-H5 (HA) antibody or a portion of the nucleic acid molecule. In another aspect, the present invention provides an isolated nucleic acid molecule encoding the variable region of the light chain of an anti-H5 (HA) antibody or a portion of the nucleic acid molecule. In another aspect, the present invention provides an isolated nucleic acid molecule encoding the CDRs of the antibody heavy chain or light chain variable regions.

Labeled Reagents

"Labeled reagent" refers to a substance comprising a detectable label attached with a specific binding member (e.g., detection probe). The attachment may be covalent or non-covalent binding, but the method of attachment is not critical to the present invention. The label allows the label reagent to produce a detectable signal that is related to the presence of analyte in the fluid sample. The specific binding member component of the label reagent is selected to directly bind to the analyte or to indirectly bind the analyte by means of an ancillary specific binding member, which is described in greater detail hereinafter. The label reagent can be incorporated into the test device at a site upstream from the capture zone, it can be combined with the fluid sample to form a fluid solution, it can be added to the test device separately from the test sample, or it can be pre-deposited or reversibly immobilized at the capture zone. In addition, the specific binding member may be labeled before or during the performance of the assay by means of a suitable attachment method.

"Label" refers to any substance which is capable of producing a signal that is detectable by visual or instrumental means. Various labels suitable for use in the present invention include labels which produce signals through either chemical or physical means. Such labels can include enzymes and substrates, chromogens, catalysts, fluorescent or fluorescent like compounds and/or particles, magnetic compounds and/or particles chemiluminescent compounds and or particles, and radioactive labels. Other suitable labels include particulate labels such as colloidal metallic particles such as gold, colloidal non-metallic particles such as selenium or tellurium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, and the like. Typically, a visually detectable label is used as the label component of the label reagent, thereby providing for the direct visual or instrumental readout of the presence or amount of the analyte in the test sample without the need for additional signal producing components at the detection sites.

Additional labels that can be utilized in the practice of the invention include, chromophores, electrochemical moieties, enzymes, radioactive moieties, phosphorescent groups, fluorescent moieties, chemiluminescent moieties, or quantum dots, or more particularly, radiolabels, fluorophore-labels, quantum dot-labels, chromophore-labels, enzyme-labels, affinity ligand-labels, electromagnetic spin labels, heavy atom labels, probes labeled with nanoparticle light scattering labels or other nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as alkaline phosphatase, horseradish peroxidase, $I^2$-galactosidase, alkaline phosphatase, β-galactosidase, or acetylcholinesterase and hapten conjugates such as digoxigenin or dinitrophenyl, or members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, a luminescent material such as luminol; light scattering or plasmon resonant materials such as gold or silver particles or quantum dots; or radioactive material include $^{14}C$, $^{123}I$, $^{124}I$, $^{125}I$, $^{131}I$, Tc99m, $^{35}S$ or $^3H$; or spherical shells, and probes labeled with any other signal generating label known to those of skill in the art. For example, detectable molecules include but are not limited to fluorophores as well as others known in the art as described, for example, in Principles of Fluorescence Spectroscopy, Joseph R. Lakowicz (Editor), Plenum Pub Corp, 2nd edition (July 1999) and the $6^{th}$ Edition of the Molecular Probes Handbook by Richard P. Hoagland.

A number of signal producing systems may be employed to achieve the objects of the invention. The signal producing system generates a signal that relates to the presence of an analyte (i.e., target molecule) in a sample. The signal producing system may also include all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. In some embodiments, the signal producing system provides a signal detectable by external means, by use of electromagnetic radiation, desirably by visual examination. Exemplary signal-producing systems are described in U.S. Pat. No. 5,508,178.

In some embodiments, nucleic acid molecules can be linked to the detection probe (e.g., antibody-linked oligonucleotides), whereby the nucleic acid functions as a label by utilizing nucleic acid labels. For example, a reagent solution or substrate comprised in a SCD can comprise detection reagents—plurality of detection and capture specific binding agents ("SBA")—comprising a plurality of oligonucleotides functioning to provide a detectable signal, whereby for a given subpopulation of SBAs (specific for a particular analyte), conjugated oligonucleotides are pre-stained with a different stain as compared to another subpopulation of antibodies (specific for a different analyte) are nucleic acid stains that bind nucleic acid molecules in a sequence independent manner. Examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red). Other detectable markers include chemiluminescent and chromogenic molecules, optical or electron density markers, etc.

As noted above in certain embodiments, labels comprise semiconductor nanocrystals such as quantum dots (i.e., Qdots), described in U.S. Pat. No. 6,207,392. Qdots are commercially available from Quantum Dot Corporation. The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. The use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations of same.

In some embodiments, a fluorescent energy acceptor is linked as a label to a detection probe. In one embodiment the fluorescent energy acceptor may be formed as a result of a compound that reacts with singlet oxygen to form a fluorescent compound or a compound that can react with an auxiliary compound that is thereupon converted to a fluorescent compound. Such auxiliary compounds can be comprised in buffers contained in an SCD and/or Test Device. In other embodiments, the fluorescent energy acceptor may be incorporated as part of a compound that also includes the chemiluminescer. For example, the fluorescent energy acceptor may include a metal chelate of a rare earth metal such as, e.g., europium, samarium, tellurium and the like. These materials are particularly attractive because of their sharp band of luminescence. Furthermore, lanthanide labels, such as europium (III) provide for effective and prolonged signal emission and are resistant to photo bleaching, thereby allowing Test Devices containing processed/reacted sample to be set aside if necessary for a prolong period of time.

Long-lifetime fluorescent europium(III) chelate nanoparticles have been shown to be applicable as labels in various heterogeneous and homogeneous immunoassays. See, e.g., Huhtinen et al. Clin. Chem. 2004 October; 50(10): 1935-6. Assay performance can be improved when these intrinsically labeled nanoparticles are used in combination with time-resolved fluorescence detection. In heterogeneous assays, the dynamic range of assays at low concentrations can be extended (1-3). Furthermore, the kinetic characteristics of assays can be improved by use of detection antibody-coated high-specific-activity nanoparticle labels instead of conventionally labeled detection antibodies (4). In homogeneous assays, europium(III) nanoparticles have been shown to be efficient donors in fluorescence resonance energy transfer, enabling simple and rapid highthroughput screening (5). Heterogeneous and homogeneous nanoparticle-label-based assays can be run with various sample matrixes, e.g., serum (3), heparin plasma (3), and mucus (S. Huopalahti, A. Valanne, T. Soukka, R. Vainionpaa, T. Lovgren, and H. Harma, University of Turku, unpublished data).

In some embodiments, a label (e.g., fluorescent label) disclosed herein, is comprised as a nanoparticle label conjugated with biomolecules. In other words, a nanoparticle can be utilized with a detection or capture probe. For example, a europium(III)-labeled nanoparticle linked to monoclonal antibodies or streptavidin (SA) to detect a particular analyte in a sample can be utilized in practice of the present invention (e.g., nanoparticle-based immunoassay). The nanoparticles serve as a substrate to which are attached the specific binding agents to the analyte and either the detection (i.e., label) or capture moiety.

In one embodiment, a Test Device comprises different pRNAs each patterned based on a specific analyte, a complementary SCD comprises a plurality of capture antibody linked to cognate pRNAs to those immobilized on the Test Device, and where said plurality comprising different subpopulation of antibodies specific for different analytes). Furthermore, the SCD reagent solution or substrate (e.g., lyophilized solid substrate) comprise detection probes, or a plurality of europium(III) labeled antibodies, consisting of the same subpopulations of antibodies specific for different analytes. Additional lanthanide labels that can be practiced in the present invention are known in the art, such as disclosed in U.S. Pat. No. 7,101,667. See also, e.g., Richardson F. S., "Terbium(III) and Europium(III) Ions as Luminescent probes and Stains for Biomolecular Systems," Chem. Rev., 82:541-552 (1982).

Therefore, depending on choice of labels, in some embodiments a signal is viewable by the unaided eye, while in other embodiments, a reader instrument is utilized in the practice of the present invention.

Capture Moieties.

In some embodiments, one member of a pair of complementary capture moieties will be bound to analyte-specific binding agent and the other member is immobilized on a line or spot, respectively. As referred to herein, the terms "capture moiety" means a binding moiety that is specific for a partner or complementary capture moeity (e.g., pRNA specific for complementary pRNA, or avidin/streptavidin-bioin).

In some embodiments, pyranosyl RNA (pRNA) is provided as a series of synthetic oligonucleotides conjugated to monoclonal antibody(s) or polyclonal antibodies in the assay system or method for detecting multiple analytes from a single sample. pRNA contains D-ribose in a pyranose form as opposed to furanose for RNA. Furthermore, the C-4' and C-2' phosphodiester linkage creates a rigid sugar-phosphate backbone resulting in rapid formation of highly stable pRNA duplexes. Rapid duplex formation contributes to non-specific cross-hybridization. In additional embodiments, an additional base, indole, is introduced to destabilize non-specific pRNA duplexes.

In some embodiments, pyranosyl RNA (pRNA) in a series of oligonucleotides conjugated to monocloclonal antibodies. A complementary pRNA strand is bound to the nitrocellulose membrane to capture the appropriate monoclonal antibody-analyte complex at the test line. Additional embodiments are disclosed in related U.S. patent application Ser. No. 11/677, 559.

Where multiplexed (i.e., multianalyte) detection is desired, a plurality of capture moieties is utilized, antibodies specific for one analyte(s) will comprise a member of one specific pair of complementary capture moieties and antibodies that specifically bind a second and different analyte(s) will comprise a member of a second and different specific pair of complementary capture moieties, and so on. Thus, in one embodiment, a plurality of different analyte(s) can be detected, where the cognate member of a pair of capture moieties is immobilized in a discrete location on a test membrane comprised in the test implement.

In various embodiments, capture moieties are comprised of an oligonucleotide, avidin, streptavidin, pyranosyl RNA (pRNA), antigen-antibody binding pair selected for high affinity, aptamer or a combination thereof. In further embodiments, an oligonucleotide is DNA or RNA. Moreover, in some embodiments a combination of different capture moieties are utilized in the same detection system of the invention. For example, a capture moiety pair for one specific analyte comprises an oligonucleotide pair, while a capture pair for a different analyte comprises a capture moiety pair comprising pRNA, or avidin or streptavidin, etc. In one embodiment, all capture moieties are pRNAs, with multiple pairs of pRNA capture moiety and pRNA partner capture moiety (e.g., one is conjugated to a specific binding agent and the cognate pRNA is immobilized on the lateral flow membrane).

In some embodiments, pRNA capture moieties/capture moiety partners are selected from but not limited to the following pRNAs

| Name | 4'-2' |
|---|---|
| 102a10-3-NH2 | TAGAACGAAG (SEQ ID NO: 1) |
| 102b10-3-NH2 | CTTCGTTCTA (SEQ ID NO: 2) |
| 119a10-1-NH2 | TCAGTGGATG (SEQ ID NO: 3) |
| 119b10-1-NH2 | CATCCACTGA (SEQ ID NO: 4) |
| 3a10-1-NH2 | GTATTGCGAG (SEQ ID NO: 5) |
| 3b10-1-NH2 | CTCGCAATAC (SEQ ID NO: 6) |
| 102a8-2-NH2 | AACGATTC |
| 102b8-2-NH2 | GAATCGTT |
| 119a8-1-NH2 | AGTGGATG |
| 119b8-1-NH2 | CATCCACT |
| 3a8-1-NH2 | GTATTGCG |
| 3b8-1-NH2 | CGCAATAC |
| 4a9-In | ATGCDCTTC |
| 4b8-In | GAADGCAT |
| 5a8 | TGATGGAC |
| 5b9-In | GTCDCATCA |
| 6a6 | CAGTAG |
| 6b6 | CTACTG |
| 8a6 | GACTCT |
| 8b6 | AGAGTC | all oligos with 4'-C12 amino and 2'-hexanol groups
Note D = Indole, a neutral base that adds specificity to the oligonucleotide.

In other embodiments, a combination of different types of capture moieties is utilized in devices and assays of the invention to detect multiple analytes (e.g., plurality of capture probes and detection probes whereby each population of capture probe and detection probe is specific for a single type of target analyte. Capture probes can be configured with one or more different capture moieties such as aptamers, pRNA or streptavidin, etc.)

Figure 4:
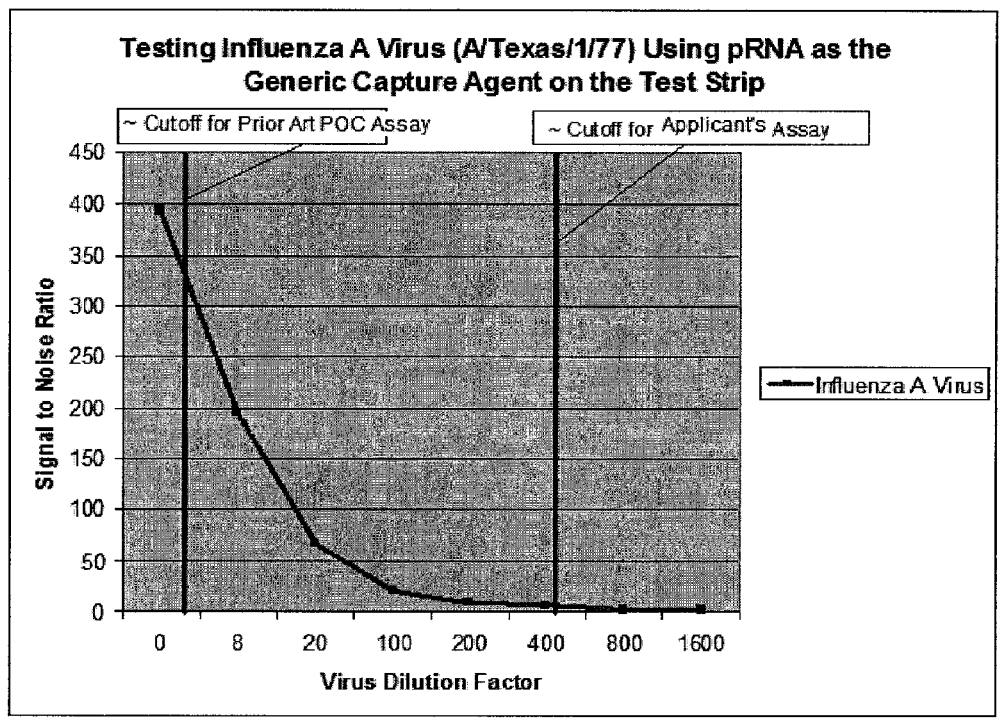
FIG. 4 illustrates one example for detection of analytes with greater sensitivity (~2 logs improvement over prior art) and specificity.

In one embodiment, combinations capture probes utilizing pRNA capture moieties are utilized to detect a plurality of different target analytes (e.g., 1, 2, 3, 4, 5 or 6 different viral antigens). For example, as illustrated in FIG. 4 a device of the invention is used to detect a virus at a higher sensitivity.

Figure 5A:
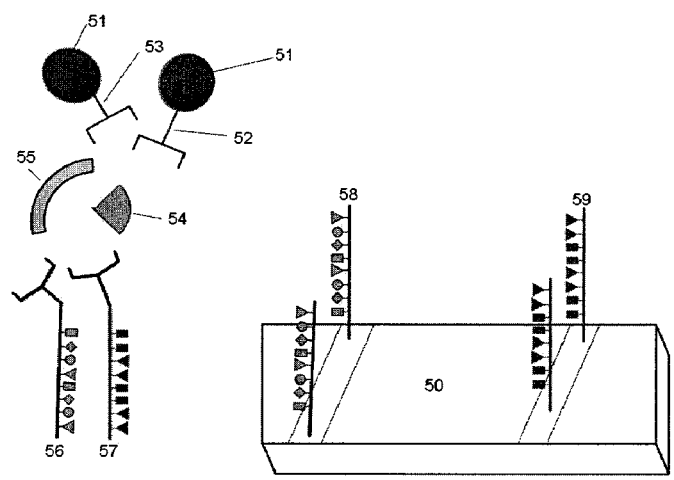
FIGS. 5A and 5B depict one embodiment of the test device.
Figure 5B:
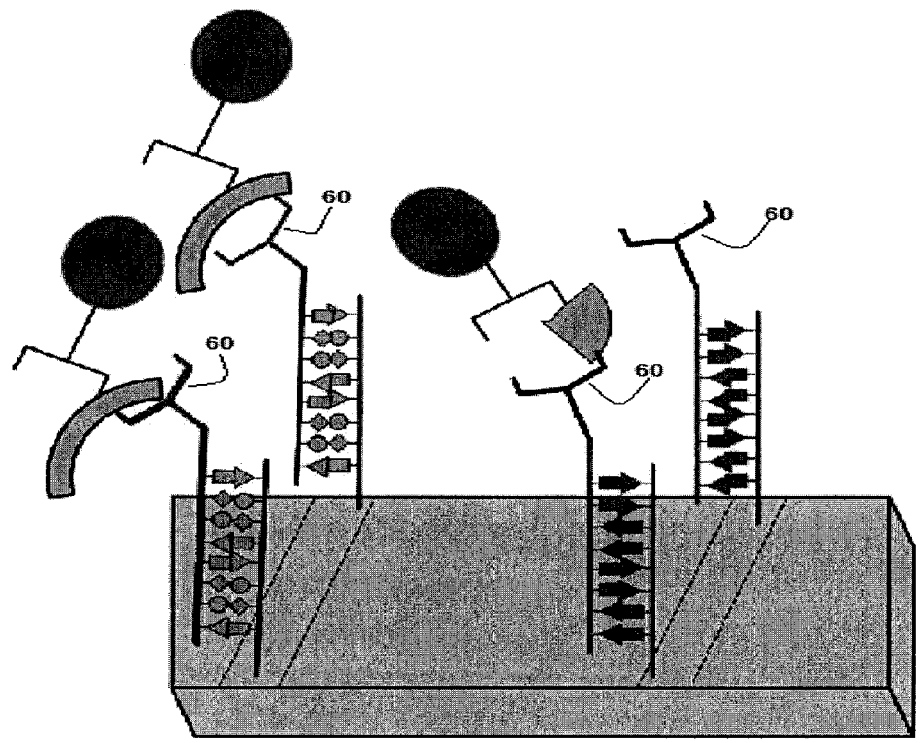

In some embodiments, a sample containing multiple analytes (e.g., 1, 2, 3, 4, 5, or more) FIG. 5A is brought into contact with capture and detection probes (e.g., FIG. 5A). Capture antibodies 60 are directed to different target analytes 54, 55 and all capture antibodies 60 specific for a particular target have a pRNA capture moiety 56, 57 which is capable of specifically binding to a immobilized capture moiety 58, 59. Therefore, where detection probes (e.g., antibody with detectable label) bind a specific target analyte, and capture probes bind a specific target analyte, the capture moieties 56, 57 provide a means to bind the target-detection probe-capture probe complex to a particular addressable line on the test device 50. In this way, a plurality of different target analytes can be detected (e.g., different pathogens, infectious agents, or types/subtypes of the same an infectious agent).

The devices and methods of the invention are configured to provide increased specificity and sensitivity to a plurality of different target analytes.

Figure 6:
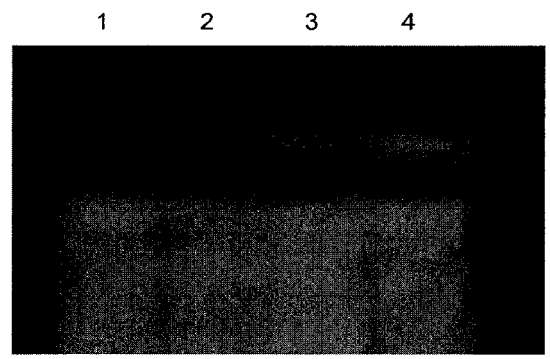
FIG. 6 illustrate one embodiment for detection of an analyte.

In other embodiments, target analyte(s) can be polypeptides or peptides associated with a subject and not an infectious agent. In yet further embodiments, target analyte(s) can be associated with a cancer, tumor or neoplasm. As illustrated in FIG. 6, a target analyte can be detected with enhanced sensitivity (FIG. 6 illustrates a peptide, NT-proBNP peptide, detected utilizing pRNA capture moiety pairs to detect 10 pg/ml (lane 2), 100 pg/ml (lane 3), 1000 pg/ml (lane 4), of NT-proBNP peptide. The control lane that did not contain any peptide (lane 1) and did not produce any detectable signal. In limited dilution assay using NT-proBNP peptide, as shown in FIG. 6, the detection limit was 0.36 pg/ml of peptide, which translates to 1.7 attamoles ($10^{-18}$) of peptide.

Therefore, where a plurality of capture probes (e.g., antibody linked to pRNA), each capture probe is linked to a capture moiety, for which a cognate capture probe is immobilized in a predetermined location on a test strip comprised in a Test Device. For example, a plurality of antibodies in an SCD is comprised of antibodies targeting different influenza virus strains and/or subtypes, where said antibodies are comprised of pairs of detection antibody-capture antibody and where the capture antibody has a specific capture moiety. Further, each population of antibodies in the plurality of antibodies is defined by the particular target analyte to which the antibody binds. Thus, all capture antibodies directed to one specific target analyte will have the same capture moiety, for which cognate/complementary capture moieties are disposed in the Test Device.

In some embodiments, capture moieties are aptamer molecules that are can be interchangeably utilized with a capture probe or as an immobilized capture moiety included in the Test Device axial flow membrane. Aptamers include nucleic acids that are identified from a candidate mixture of nucleic acids. In a preferred embodiment, aptamers include nucleic acid sequences that are substantially homologous to the nucleic acid ligands isolated by the SELEX method. Substantially homologous is meant a degree of primary sequence homology in excess of 70%, most preferably in excess of 80%. The "SELEX" methodology, as used herein, involves the combination of selected nucleic acid ligands, which interact with a target analyte in a desired action, for example binding to a protein, with amplification of those selected nucleic acids. Optional iterative cycling of the selection/amplification steps allows selection of one or a small number of nucleic acids, which interact most strongly with the target antigen/biomarker from a pool, which contains a very large number of nucleic acids. Cycling of the selection/amplification procedure is continued until a selected goal is achieved. The SELEX methodology is described in the following U.S. patents and patent applications: U.S. patent application Ser. No. 07/536,428 and U.S. Pat. Nos. 5,475,096 and 5,270,163.

Analytes

In one aspect of the invention, one or more analytes are detected using the device, system and methods of the invention. In various embodiments, one or more analytes include but are not limited to one or more mammalian cell, virus, bacteria, yeast, fungi, parasite, components of the preceding, nucleic acid, polypeptide, peptide, and combinations thereof.

In various embodiments, the analyte(s) detected are associated with an infectious agent. An infectious agent can be any pathogen including without any limitation bacteria, yeast, fungi, virus, eukaryotic parasites, etc. In some embodiments, the infectious agent is influenza virus, parainfluenza virus, adenovirus, rhinovirus, coronavirus, hepatitis viruses A, B, C, D, E, etc, HIV, enterovirus, papillomavirus, coxsackievirus, herpes simplex virus, or Epstein-Barr virus. In other embodiments, the infectious agent is *Mycobacterium, Streptococcus, Salmonella, Shigella, Staphylococcus, Neisseria, Clostridium*, or *E. coli*. It will be apparent to one of skill in the art that the compositions and methods of the invention are readily adaptable to different infectious agents, by utilizing a different panel of binding agents (e.g., antibodies) that are specific for type(s) or subtype(s) of an infectious agent(s).

Usually the general type of an infectious agent can be the genus type of an infectious agent or any primary or first instance typing or identification of an infectious agent. A subtype of an infectious agent can be the species or strain type of an infectious agent or any secondary or subsequent typing of an infectious agent. According to the present invention, identification of the general type or subtype of an infectious agent can be carried out via various suitable test set ups. For example, identification of the general type of an infectious agent can include one or more screening tests for 1) a specific general type of an infectious agent, 2) certain desired or selected general types of an infectious agent, or 3) all or substantially all relevant general types of an infectious agent, or a combination thereof. Similarly identification of the subtype of an infectious agent can include one or more screening tests for 1) one or more specific subtypes of an infectious agent, 2) one or more specific subtypes of a particular general type of an infectious agent, 3) one or more specific subtypes of an infectious agent selected based on additional information associated with the subject being tested, e.g., one or more suspected or expected subtypes for a particular population or geographic location or 4) one or more potentially pandemic or epidemic subtypes of an infectious agent that is identical to or associated with the infectious agent tested for the general type, or a combination thereof.

In particular, the general type of an influenza virus can be any type designated based on antigenic characteristics of the nucleoprotein and matrix protein antigens, e.g., type A, B, or C influenza virus, whereas the subtype can be one or more subdivided types of an influenza virus on the basis of an antigen, e.g. one or more subtypes of influenza type A or type B virus characterized by a surface antigen such as hemagglutinin (H) or neuraminidase (N).

In one embodiment, identification of the general type of influenza virus includes screening for type A, type B, and/or type C influenza virus whereas identification of the subtype of influenza virus, e.g., type A virus includes screening for one or more expected subtypes of type A, e.g., subtypes expected to be present in the population at the time of testing, and optionally one or more suspected subtypes, e.g., subtypes under surveillance for an outbreak such as epidemic or pandemic outbreak. In another embodiment, identification of the general type of influenza virus includes screening for type A and type B influenza virus whereas identification of the subtype of influenza virus, e.g., type A virus includes screening for one or more subtypes used for the production of the influenza vaccine, e.g., current vaccine subtypes(s) or strain(s) for the testing season including subtypes and/or strains expected to be in circulation during the next influenza season. In yet another embodiment, identification of the general type of influenza virus includes screening for type A and type B influenza virus whereas identification of the subtype of influenza virus, e.g., type A includes screening for one or more subtype(s) or strain(s) used for the production of the influenza vaccine and one or more subtype(s) or strain(s) suspected for the cause of a pandemic outbreak, e.g., one or more avian subtype(s) or strain(s) such as H5N1 or the derivatives thereof.

In one embodiment, the methods and compositions of the invention can be utilized in assays to detect *E. coli* 0157 (a very dangerous, often fatal infectious strain) in the presence of other enteric or infective strains. Another example would be in testing patients for influenza infection, where mutation or variation of the strains within subtypes is known to occur and some forms of influenza are far more pathogenic than others. A further example is detection of different types of HIV, for example HIV-1 and HIV-2.

In one embodiment, the methods and apparatus of the invention are utilized to detect or identify an influenza type A subtype and/or influenza type B.

Influenza virus belongs to the genus orthomyxovirus in the family of Orthomyxoviridae. ssRNA enveloped viruses with a helical symmetry. Enveloped particles 80-120 nm in diameter. The RNA is closely associated with the nucleoprotein (NP) to form a helical structure. The genome is segmented, with 8 RNA fragments (7 for influenza C). There are 4 principle antigens present, the hemagglutinin (H), neuraminidase (N), nucleoprotein (NP), and the matrix (M) proteins.

The NP is a type-specific antigen which occurs in 3 forms, A, B and C, which provides the basis for the classification of human and non-human influenza viruses. The matrix protein (M protein) surrounds the nucleocapsid and makes up 35-45% of the particle mass. Furthermore, 2 surface glycoproteins are seen on the surface as rod-shaped projections. The haemagglutinin (H) is made up of 2 subunits, H1 and H2. Haemagglutinin mediates the attachment of the virus to the cellular receptor. Neuraminidase molecules are present in lesser quantities in the envelope. The antigenic differences of the hemagglutinin and the neuraminidase antigens of influenza A viruses provide the basis of their classification into subtypes. e.g., A/Hong Kong/1/68 (H3N2) signifies an influenza A virus isolated from a patient in 1968, and of subtype H3N2.

In various embodiments, the methods and apparatus of the invention are directed to detecting or identifying influenza virus type A which is defined by HxNy where x is 1-9 and y is 1-16, or any combination of xy thereof. For example, in one embodiment, the methods and apparatus of the invention is utilized to detect influenza A subtype H1N5. Thus, a plurality of detection probes and capture probes targeting different subtypes of influenza virus are disposed in an SCD of the invention. In one embodiment, the assay is utilized to detect Influenza A (with subtypes H1/H3, and a pandemic subtype H5) and Influenza B.

In various embodiments, methods and apparatus of the invention can detect one or more different infectious agents. For example, a sampling implement can comprise a plurality of different antibodies, wherein multiple subgroups of antibodies are present, whereby each subgroup of antibodies specifically binds a different infectious agent. For example, a plurality of antibodies can comprise 2, 3, 4, 5, 6, 7, 8, 9 or 10 subgroups, wherein each subgroup of antibodies in the plurality of antibodies specifically binds a different infectious agent. In some embodiments, methods and apparatus of the invention detect a pandemic and non-pandemic infectious agent. In one embodiment, the pandemic and non-pandemic infectious agents are influenza virus.

The explosive nature of epidemic influenza and the specific clinical features of this disease have given reliable epidemiological records of this infection since the beginning of the nineteenth century. Several epidemics were recorded during the nineteenth century but the first pandemic was not accurately recorded until 1889-92. A second pandemic, probably originating in Europe, occurred in 1918-19, and is known as Spanish Influenza, which was responsible for 20-25 million deaths, principally in young adults.

Pandemics continued to occur regularly after the Spanish influenza, in 1932-33, 1947-48, 1957 and 1968. The next pandemic is thought to be overdue. These latter pandemics resembled the pandemic of 1890, affecting millions of people with a mild URTI and a small number of deaths. The H1N1 (swine) viruses probably appeared in 1918 and continued to circulate until 1957, at which time they were supplanted by the H2N2 (Asian) viruses. The H2N2 viruses were prevalent until 1968, when H3N2 (Hong Kong) strains appeared. The H1N1 virus reappeared in 1977 and did not replace the H3N2 subtype and both subtypes continued to cocirculate. Therefore, it is imperative that subjects are screened in an effective and accurate manner to determine with what strain and/or subtype an individual is infected. Furthermore, in some circumstances such sample collection and processing will necessarily occur in a point-of-care setting (e.g., in the field, without large numbers of subjects to sample and process, and with limited man power to effect such sampling).

As such, in one embodiment, the methods and apparatus of the invention are utilized in processing a large number of samples, in a point-of-care setting, where test results may be visualized (i.e., read) some period of time after the test is complete. For example, the period of time can be 30 minutes, 1 hour, 1.5 hour, 2 hours, 2.5 hours, 3 hours, 4 hours or 5 hours. In some embodiments, methods and apparatus in conjunction with the reagents disclosed herein provide high sensitivity and specificity where the fluorescent result can be read with very similar results over a long period of time. Thus, in some embodiments biological samples can be collected and processed, but set aside to be read a significant time later, which is greatly advantageous in point-of-care settings or where a large number of samples are collected with limited manpower or time to further process samples.

In various embodiments, analytes detected are one or more biomarkers which are indicative of a disease, condition or predisposition to a disease or condition. Examples of such analytes include but are not limited to tumor antigens, peptides indicative of stroke, peptides indicative of hear failure heart failure, peptides indicative of pre-clampsia, eclampsia, liver damage or disease, kidney damage or disease, heart damage or disease, brain damage or disease, or any combination thereof.

In various embodiments, detection of markers (also biomarkers) can be before during or after treatment, and as such, detection of one or more markers is used to assess the efficacy of or a subject's response to a treatment regimen.

In various embodiments, devices and methods of the invention are configured to detect one or more markers (e.g., peptides or antigens) associated with any condition or disease. For example, one or more markers can be detected which are associated with any disease or condition, including but not limited to a cancer or tumor, a heart condition, damage or disease, a brain condition, liver condition, damage or disease, kidney condition, damage or disease, or a combination thereof. In further embodiments, detection of one or more markers is before, during or after treatment of a subject with a therapeutic agent. Thus, a treatment regimen for a subject or population of subjects can be assessed to determine the efficacy of a therapeutic regimen. In yet other embodiments, markers associated with one or more adverse or negative effects can be detected to determine the incidence or severity of adverse effects. In yet other embodiments, one or more markers are detected to diagnose a disease or condition.

Example of detection markers can be tumor antigens associated with cancer. Examples of such tumor cell components include, but are not limited to, epidermal growth factor receptor (EGFR, ErbB-1, HER1), ErbB-2 (HER2/neu), ErbB-3/HER3, ErbB-4/HER4, EGFR ligand family, insulin-like growth factor receptor (IGFR) family, IGF-binding proteins (IGFBPs), IGFR ligand family, platelet derived growth factor receptor (PDGFR) family, PDGFR ligand family, fibroblast growth factor receptor (FGFR) family, FGFR ligand family, vascular endothelial growth factor receptor (VEGFR) family, VEGF family, HGF receptor family, TRK receptor family, ephrin (EPH) receptor family, AXL receptor family, leukocyte tyrosine kinase (LTK) receptor family, TIE receptor family, angiopoietin 1,2, receptor tyrosine kinase-like orphan receptor (ROR) receptor family, discoidin domain receptor (DDR) family, RET receptor family, KLG receptor family, RYK receptor family, MuSK receptor family, Transforming growth factor beta (TGF-β), e.g., three isoforms called TGF-β, TGF-β2 and TGF-β3; Cytokine receptors, Class I (hematopoietin family) and Class II (interferon/IL-10 family) receptors, tumor necrosis factor (TNF) receptor superfamily (TNFRSF), death receptor family (Apo2L/TRAIL-Receptors, CD95/Fas), cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), β-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: β-Dgalactose 2-α-Lfucosyltransferase (LDLR/FUT) fusion protein, HLA-A2. arginine to isoleucine exchange at residue 170 of the α-helix of the α2-domain in the HLA-A2 gene (HLA-A*201-R170I), HLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class I, NFYC, OGT, OS-9, pml-RARalpha fusion protein, PRDX5, PTPRK, K-ras (KRAS2), N-ras (NRAS), HRAS, RBAF600, SIRT2, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGAT5), HERV-K-MEL, KK-LC, KM-HN-1, LAGE, LAGE-1, CTL-recognized antigen on melanoma (CAMEL), MAGE-A1 (MAGE-1), MAGE-A2, MAGE-A3, MAGE-A4, MAGE-A5, MAGE-A6, MAGE-A8, MAGE-A9, MAGE-A10, MAGE-A11, MAGE-A12, MAGE-3, MAGE-B1, MAGE-B2, MAGE-B5, MAGE-B6, MAGE-C1, MAGE-C2, mucin 1 (MUC1), MART-1/Melan-A (MLANA), gp100, gp100/Pmel17 (SILV), tyrosinase (TYR), TRP-1, HAGE, NA-88, NY-ESO-1, NY-ESO-1/LAGE-2, SAGE, Sp17, SSX-1, 2, 3, 4, TRP2-INT2, carcino-embryonic antigen (CEA), Kallikrein 4, mammaglobin-A, OA1, prostate specific antigen (PSA), TRP-1/gp75, TRP-2, adipophilin, interferon inducible protein absent in melanoma 2 (AIM-2), BING-4, CPSF, cyclin D1, epithelial cell adhesion molecule (Ep-CAM), EphA3, fibroblast growth factor-5 (FGF-5), glycoprotein 250 (gp250), EGFR (ERBB1), HER-2/neu (ERBB2), interleukin 13 receptor α2 chain (IL13Ralpha2), IL-6 receptor, intestinal carboxyl esterase (iCE), alpha-feto protein (AFP), M-CSF, mdm-2, MUC1, p53 (TP53), PBF, PRAME, PSMA, RAGE-1, RNF43, RU2AS, SOX10, STEAP1, survivin (BIRC5), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA661, LDHC, MORC, SGY-1, SPO11, TPX1, NY-SAR-35, FTHL17, NXF2, TDRD1, TEX15, FATE, TPTE, immunoglobulin idiotypes, Bence-Jones protein, estrogen receptors (ER), androgen receptors (AR), CD40, CD30, CD20, CD19, CD33, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), β-human chorionic gonadotropin, β-2 microglobulin, squamous cell carcinoma antigen, neuron-specific enolase, heat shock protein gp96, GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), Human papilloma virus (HPV) proteins (HPV-E6, HPV-E7, major or minor capsid antigens, others), Epstein-Barr virus (EBV) proteins (EBV latent membrane proteins—LMP1, LMP2; others), Hepatitis B or C virus proteins, and HIV proteins.

In other embodiments, detection markers peptides or cell components associated with a disease, condition, or organ damage. Examples of such markers include, but are not limited to those disclosed in U.S. Pat. No. 7,361,473, such as brain natriuretic peptide (BNP), NT-proBNP, proBNP, CNP, and ANP, cardiac troponins, C reactive protein, lipolipoprotein A, NCA 50/90, 36P6D5, glutathione-S-transferase P1 (GSTP1), lipoproterin associated cholesterols, HLLRCR-1, KIR4.1, brain associated human glutamine synthetase or matrix metalloproteins, and variants thereof, including but not limited to markers disclosed in U.S. Pat. Nos. 5,605,894, 6,709,818, 6,028,055, 7,223,542, 7,332,569, 7,348,149, 7,262,290, or 7,070,945 and WO/2005/072055.

Figure 7:
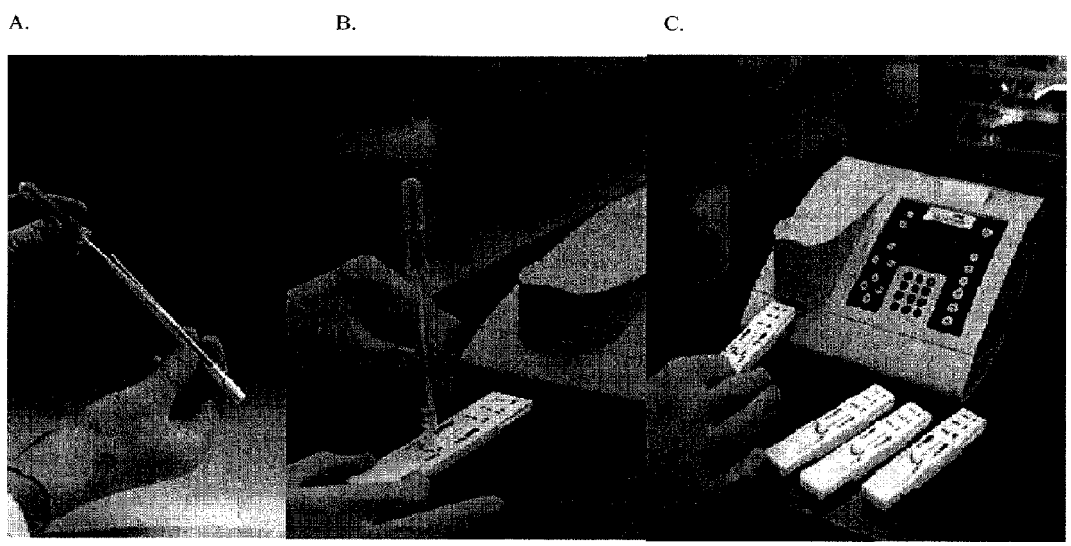
FIG. 7A-C illustrate one embodiment of work flow for processing a sample using a detection system.
Figure 8:
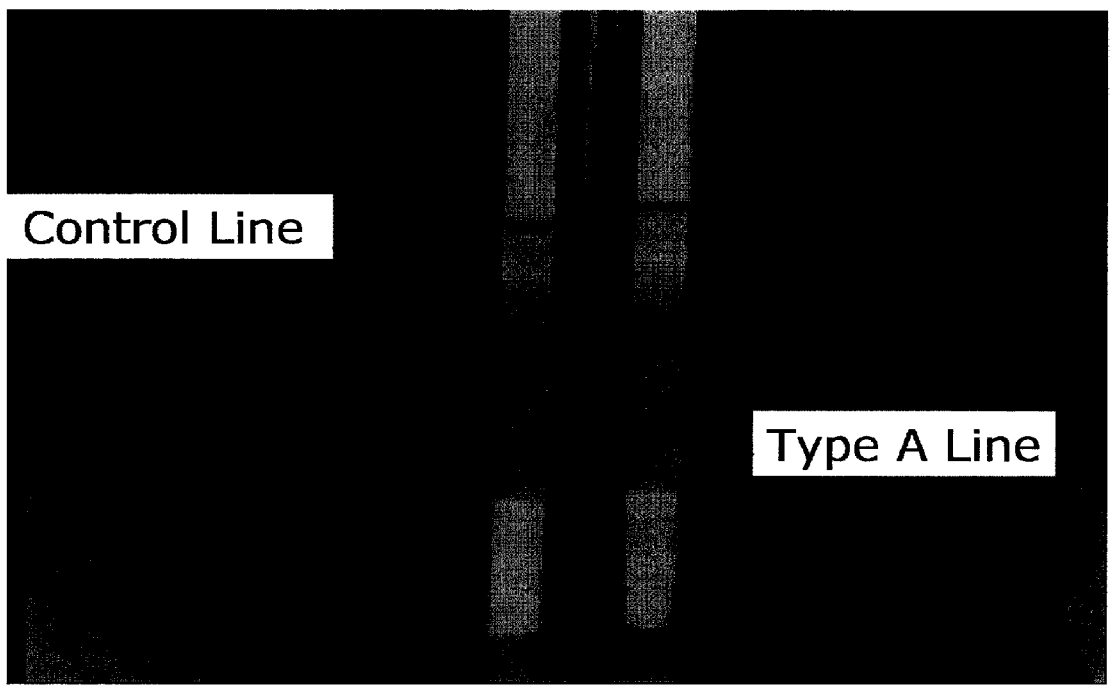
FIG. 8 illustrates a strip/dipstick example for detection influenza.
Figure 9:
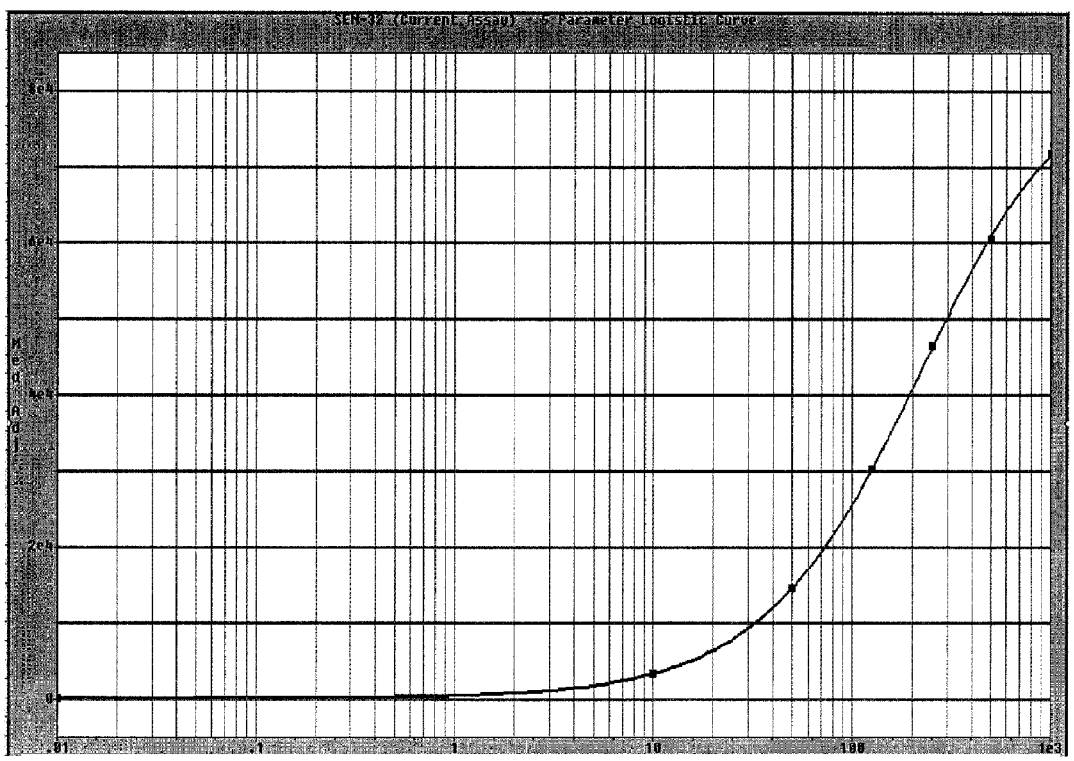
FIG. 9 illustrates a NT-proBNP standard curve.

Work Flow:

In general, a sample is processed using an SCD of the invention which prepares a sample for application to a TD and reading a result via a Reader, as illustrated in FIG. 7. For example, in some embodiments, a sample is obtained or added to a SCD FIG. 7(A) and one or more analytes are contacted with reagents present in the SCD (e.g., detection and capture probes, and/or extraction reagents). The sample is then processed through the SCD to the TD as illustrated in FIG. 7(B) and read on a optical reader FIG. 7(C). For example, the sampling implement can be used to swab a cell, tissue or liquid sample from a subject FIG. 7(A) where an extraction buffer (supra) is released. The SCD is then placed into a TD as illustrated in FIG. 7(B) and a bulb on the SCD is squeezed to transfer fluid from the SCD to the TD. Alternatively a buffer present in the TD (e.g., wash or running buffer with or without additional reagents, dyes, labels) is released once the snap button FIG. 2 on the TD is pressed. Subsequently or a substantial time thereafter the TD is inserted into an optical reader to detect presence of a detectable signal at one or more defined lines on the TD. In some embodiments, the TD is read in about 5, 10, 15, 20, 30, 40, 50 or 60 minutes. However, if necessary (e.g., operator has multiple TDs to process) the TD is configured to provide accurate reads from several hours (e.g., 1, 2, 3, 4, 5, 6, 7, 8, 9, 10, 11, 12, 13, 14, 15, 16, 17, 18, 19, 20, 21, 22, 23, 24 hours) or to a few days after running the sample (e.g., 1, 2, 3, 4, 5, 6 or 7 days). As discussed in the In one embodiment, after the health care worker collects a specimen a sampling implement (e.g., swab) is inserted part way into the plastic tube and the handle of the swab is broken off and discarded. The handle of the SCD with the extraction reagents is affixed to the tube, the valve broken, the bulb squeezed to move the fluid to the swab tip (e.g., FIG. 7A).

In one embodiment, a sample is collected from a subject via a sampling implement and placed back into the cylinder housing of the SCD device (e.g., FIG. 7). The SCD can first be inserted into a Test Device, or prior to insertion into a Test Device, a solution contained in the upper sealed chamber of the SCD is released to effect washing the sample and solution into a mixture downwards into a reaction chamber. In the reaction chamber is disposed either liquid or solid reagents comprising detection and capture probes that target one or more different analytes as disclosed herein, thereby forming a complex of analyte bound to detection and capture probe. The sample is then expelled from the SCD into a Test Device through an aperture that seals the contact between the SCD and the Test Device from the outside environment (e.g., preventing any spillage, aerosol or contamination). The sample mixture can flow as a result of gravity or the force of air pressure produced by squeezing the SCD (e.g., upper sealed chamber), into a Test Device. The sample is driven by capillary force and/or by wash buffer comprised in the Test Device so as to allow any analyte-probe complex to pass through the lateral flow membrane contained in the Test Device. Capture probes and complementary immobilized capture moieties bind or hybridize to each other in predetermined lines or spots on the lateral flow membrane, whereby detection probes (via conjugate labels contained thereon) will provide a detectable signal which can subsequently be read to determine which analytes were present in the sample processed.

In one embodiment, Test Devices with samples processed thereon, can be set aside for time periods of about 1, 2, 3, 4, 5, 6 or 8 hours before reading the results, and yet provide results as accurately as if read in 15 or 20 minutes after processing. Thus, the signals produced are stable for long periods of time so that reading the results may occur at a significantly later time after the tests are actually performed. This is a great improvement for point-of-care diagnostics, where in the field conditions often present limited resources in manpower and time, and where the test setting can be in remote regions that are not easily or quickly accessed.

For example, the cap is removed and the SCD is attached to the TD. The bulb is squeezed again. The extracted sample dissolves the reagent bead and the mixture is transferred to the wicking pad of the TD. The button on the TD is depressed starting the flow of wash buffer.

The TD is placed into the reader. The operator enters their ID into the reader and depresses the "start" button. No other operator interaction with the reader is required other than to remove the TD from the reader. The reader will automatically display and print the result and with the addition of communication connectivity capability the system will make the result available to be downloaded.

EXAMPLES

Example 1

Detecting Different Influenza Types/Subtypes

Assay was performed on the following influenza strains according to the guidelines set by the Center for Disease Control; New Calcdonia/20/99 H1N1 influenza A, Hawaii/15/01 H1N1 influenza A, New York/55/04 H3N2 influenza A, Wisconsin/67/05/ H3N2 influenza A, Florida/07/06 influenza B, Ohio/15/01 influenza B, an H5 influenza A, and an H5 influenza V. Each strain was diluted to 1:100, 1:750, 1:1000, 1:7,500, or 1:10,000 for testing the sensitivity of the assay system. Normalized test results were presented in Table 1, showing test results of on various influenza strains, demonstrating the assay can clearly distinguish between Type A, TypeB, H1/H3 (detected together), and H5.

Example 2

Assay Specificity

To test whether the POC assay system can stringently identify influenza strains in samples including non-influenza bacteria and virus, the following microorganisms were tested for the possibility of giving false positive signals; *K. oxytoca, P. aeruginosa, P. mirabilis, S. aureus, S. aureus*-303802, *S. maltophilia, S. marcescens, S. simulans*, Cytomegalovirus culture fluid, Herpes simplex virus culture fluid, Epstine B virus culture fluid, Parainfluenza culture, Coxsackievirus culture, Echovirus culture, Coronavirus culture Rous sarcoma virus culture, and Adenovirus culture. Normalized results were presented in Table 2, demonstrating assay specificity with respect to cross reactivity with non-influenza bacteria and virus.

TABLE 1

| Virus | Dilution | Control | H5 | H1/H3 | Flu B | Flu A |
|---|---|---|---|---|---|---|
| A/New Caledonia/20/99 (H1N1) | 1:100 | 16.39 | 0.00 | 6.73 | 0.05 | 40.38 |
| 1:100 TCID50 titer 4.6 | 1:1000 | 17.39 | 0.00 | 0.61 | 0.25 | 4.76 |
| End point titer: ~600 | 1:7500 | 16.28 | 0.00 | 0.00 | 0.08 | 0.92 |
| | 1:7500 | 14.44 | 0.00 | 0.20 | 0.28 | 0.94 |
| | 1:10000 | 15.48 | 0.00 | 0.00 | 0.00 | 1.02 |
| A/Hawaii/15/2001 (H1N1) | 1:100 | 15.53 | 0.00 | 0.63 | 0.23 | 38.23 |
| 1:100 TCID50 titer 4.7 | 1:750 | 13.73 | 0.00 | 0.41 | 0.00 | 9.41 |
| End point titer: ~700 | 1:1000 | 16.12 | 0.00 | 0.00 | 0.00 | 7.56 |
| | 1:7500 | 15.48 | 0.00 | 0.00 | 0.00 | 1.13 |
| | 1:10000 | 15.49 | 0.02 | 0.13 | 0.00 | 0.97 |
| A/New York/55/2004 (H3N2) | 1:1000 | 23.10 | 0.00 | 1.17 | 0.14 | 11.37 |
| 1:100 TCID50 titer 3.5 | 1:7500 | 15.02 | 0.00 | 0.26 | 0.12 | 1.61 |
| End point titer: ~10 | 1:7500 | 15.53 | 0.00 | 0.16 | 0.30 | 1.86 |
| | 1:10000 | 16.57 | 0.00 | 0.00 | 0.22 | 1.48 |
| | 1:10000 | 16.67 | 0.00 | 0.11 | 0.00 | 1.88 |
| A/Wisconsin/67/2005 (H3N2) | 1:100 | 15.53 | 0.10 | 2.76 | 0.17 | 56.34 |
| 1:100 TCID50 titer 4.6 | 1:750 | 15.67 | 0.00 | 0.76 | 0.00 | 11.12 |
| End point titer: ~300 | 1:1000 | 16.58 | 0.00 | 0.47 | 0.00 | 9.09 |
| | 1:7500 | 15.33 | 0.00 | 0.09 | 0.02 | 1.42 |
| | 1:10000 | 20.98 | 0.00 | 0.00 | 0.00 | 1.33 |
| B/Florida/07/2006 | 1:100 | 16.08 | 0.00 | 0.16 | 12.81 | 0.36 |
| 1:100 TCID50 titer 4.5 | 1:1000 | 17.11 | 0.11 | 0.33 | 1.34 | 0.24 |
| End point titer: ~250 | 1:7500 | 16.95 | 0.05 | 0.17 | 0.19 | 0.25 |
| | 1:7500 | 15.62 | −0.30 | 0.26 | 0.14 | 0.00 |
| | 1:10000 | 16.49 | 0.00 | 0.00 | −0.05 | 0.24 |
| B/Ohio/15/2001 | 1:1000 | 22.09 | 0.00 | 0.00 | 11.26 | 0.42 |
| 1:100 TCID50 titer 3.5 | 1:7500 | 18.66 | 0.00 | 0.08 | 2.35 | 0.36 |
| End point titer: ~10 | 1:10000 | 16.99 | 0.00 | 0.00 | 1.83 | 0.30 |
| | 1:10000 | 15.88 | 0.00 | 0.00 | 2.16 | 0.44 |
| | 1:75000 | 16.19 | 0.00 | 0.60 | 0.51 | 0.58 |
| H5 A | 1:100 | 13.32 | 1.17 | 0.35 | 0.23 | 79.50 |
| 1:100 TCID50 titer 5.7 | 1:750 | 15.13 | 0.00 | 0.00 | 0.04 | 33.89 |
| End point titer: ~700 | 1:1000 | 15.01 | 0.00 | 0.14 | 0.00 | 29.15 |
| | 1:7500 | 15.73 | 0.00 | 0.07 | 0.00 | 4.78 |
| | 1:10000 | 15.57 | 0.00 | 0.00 | −0.01 | 3.58 |
| H5 V | 1:100 | 14.20 | 1.40 | 0.40 | 0.21 | 72.24 |
| 1:100 TCID50 titer 5.7 | 1:750 | 15.47 | 0.00 | 0.00 | −0.04 | 22.37 |
| End point titer: ~700 | 1:1000 | 15.67 | 0.00 | 0.00 | −0.11 | 19.89 |
| | 1:7500 | 15.89 | 0.00 | 0.04 | 0.32 | 2.86 |
| | 1:10000 | 16.08 | 0.00 | 0.00 | 0.00 | 2.86 |
| No Virus Control 1 | | 16.58 | −1.08 | 0.14 | 0.00 | 0.28 |
| No Virus Control 2 | | 15.59 | 0.00 | 0.00 | 0.00 | 0.18 |
| No Virus Control 3 | | 14.43 | 0.38 | 0.00 | 0.40 | 0.33 |
| No Virus Control 4 | | 16.00 | −0.74 | 0.40 | −0.03 | 0.08 |

TABLE 2

| Sample Name | Control | H5 | H1/H3 | Flu B | Flu A | Call |
|---|---|---|---|---|---|---|
| TBS/Casein/NaN3-1 | 17.39 | 0.09 | 0.22 | 0.04 | 0.00 | Neg |
| TBS/Casein/NaN3-2 | 17.87 | 0.03 | 0.33 | 0.20 | −0.03 | Neg |
| H. influenzae | 18.30 | 0.00 | 0.03 | 0.11 | 0.00 | Neg |
| K. oxytoca | 17.76 | 0.34 | 0.59 | 0.41 | 0.38 | Neg |
| P. aeruginosa | 13.42 | 0.21 | 0.48 | 0.37 | 0.32 | Neg |
| P. mirabilis | 18.26 | 0.00 | 0.34 | 0.25 | 0.33 | Neg |
| S. aureus | 17.85 | 0.17 | 0.19 | 0.00 | 0.03 | Neg |
| S. aureus-303802 | 14.24 | 0.00 | 0.75 | 0.00 | 0.95 | Neg |
| S. maltophilia | 17.36 | 0.12 | 0.01 | 0.01 | 0.22 | Neg |
| S. marcescens | 16.34 | 0.00 | 0.20 | 0.09 | 0.20 | Neg |
| S. simulans | 17.63 | 0.00 | 0.17 | 0.13 | 0.35 | Neg |
| CMV Culture Fluid | 17.35 | 0.00 | 0.04 | 0.02 | 0.02 | Neg |
| HSV Culture Fluid | 5.39 | 0.10 | 0.20 | 0.08 | 0.08 | Neg |
| EBV Culture Fluid | 17.69 | 0.33 | 0.44 | 0.29 | 0.23 | Neg |
| Parainfluenza Culture | 18.26 | 0.00 | 0.02 | 0.18 | −0.02 | Neg |
| Coxsackievirus Culture | 17.34 | 0.00 | 0.37 | 0.31 | 0.51 | Neg |
| Echovirus Culture | 15.70 | 0.32 | 0.38 | 0.44 | 0.02 | Neg |

TABLE 2-continued

| Sample Name | Control | H5 | H1/H3 | Flu B | Flu A | Call |
|---|---|---|---|---|---|---|
| Coronavirus Culture | 17.40 | 0.15 | 0.02 | 0.10 | 0.06 | Neg |
| RSV Culture | 14.98 | 0.51 | 0.23 | 0.14 | 0.05 | Neg |
| Adenovirus Culture | 13.98 | 0.00 | 0.00 | 0.22 | 0.12 | Neg |

Example 3

Drug Interference

To test whether the POC assay system can identify influenza virus from samples containing drugs commonly taken for influenza infection, the following drugs were added in the sample containing H1N1 influenza A in following specified doses; 10 mg/ml of, Tylenol, 10 mg/ml of Bayer Aspirin, 10 mg/ml of Advil, 5 mg/ml of Bromphen, 5 mg/ml of Chlor Trimeton, 2.5 mg/ml of Symmetrel, 1 mg/ml of Ventolin, 10 mg/ml of Tussin, 10 mg/ml of Echinacea, 5 mg/ml of Galphimia G, 5 mg/ml of Histamine HC, 5 mg/ml of Oscillococcinum, 10 mg/ml of Sucrets Menthol. Normalized test results were presented in Table 3, showing test results of the assay system on interference with common drugs that might be taken during an influenza infection, demonstrating unhindered assay performance in the presence of influenza drugs in test sample.

TABLE 3

| Virus Present | Final Conc. IntSub (mg/mL) | Sample | Control | H5 | H1/H3 | B | A |
|---|---|---|---|---|---|---|---|
| +V | | Positive Control 1st | 14.86 | 0.05 | 66.28 | 0.20 | 68.52 |
| +V | | Positive Control 2nd | 14.14 | 0.09 | 72.28 | 0.02 | 59.89 |
| +V | 10 | Tylenol | 12.59 | 0.35 | 50.22 | 1.08 | 57.44 |
| +V | 10 | Bayer | 14.95 | 0.00 | 8.64 | 0.35 | 52.17 |
| +V | 10 | Advil (retest) | 13.66 | 0.26 | 8.58 | 0.08 | 49.64 |
| +V | 5 | Bromphen | 10.04 | 0.54 | 30.01 | 0.15 | 45.79 |
| +V | 5 | Chlor Trimeton | 9.50 | 0.08 | 23.02 | 0.10 | 47.50 |
| +V | 2.5 | Symmetrel | 8.58 | 0.00 | 44.93 | 0.00 | 53.20 |
| +V | 1 | Ventolin | 8.31 | 0.12 | 64.67 | 0.00 | 59.37 |
| +V | 10 | Tussin | 8.86 | 0.00 | 49.02 | 0.22 | 51.68 |
| +V | 10 | Echinacea | 17.05 | 0.00 | 64.78 | 0.00 | 5.41 |
| +V | 5 | Galphimia G | 9.34 | 0.10 | 53.30 | 0.17 | 40.94 |
| +V | 5 | Hist. HC | 9.13 | 0.14 | 44.05 | 0.00 | 42.03 |
| +V | 5 | Oscillococcinum | 11.69 | 0.00 | 80.79 | 0.00 | 50.07 |
| +V | 10 | Sucrets Menthol | 13.00 | 0.00 | 33.90 | 0.15 | 53.55 |
| +V | 10 | Benadryl | 0.38 | 0.20 | 0.53 | 0.30 | 3.03 |
| +V | 1 | Benadryl | 9.23 | 0.26 | 52.27 | 0.08 | 63.32 |
| +V | 0.1 | Benadryl | 11.20 | 0.13 | 40.33 | 0.00 | 51.65 |
| +V | 0.01 | Benadryl | 13.48 | 0.08 | 42.48 | 0.00 | 45.24 |
| −V | | Negative Control 1st | 16.95 | 0.12 | 0.67 | 0.32 | 0.84 |
| −V | | Negative control 2nd | 13.32 | 0.00 | 0.16 | 0.07 | 0.06 |
| −V | 10 | Tylenol | 17.51 | 0.50 | 0.89 | 0.29 | 0.90 |
| −V | 10 | Bayer | 8.86 | 0.11 | 0.06 | 0.07 | 0.02 |
| −V | 10 | Advil (retest)* | 20.89 | 0.00 | 0.45 | 0.48 | 0.71 |
| −V | 5 | Bromphen | 12.26 | 0.21 | 0.26 | 0.10 | 0.04 |
| −V | 5 | Chlor Trimeton | 12.95 | 0.00 | 0.80 | 0.69 | 0.18 |
| −V | 2.5 | Symmetrel | 12.04 | 0.22 | 0.19 | 0.07 | 0.04 |
| −V | 1 | Ventolin | 14.29 | 0.00 | 0.22 | 0.25 | 0.40 |
| −V | 10 | Tussin | 18.58 | 0.00 | 0.14 | 0.20 | 0.02 |
| −V | 10 | Echinacea | 15.93 | 0.00 | 0.21 | 0.20 | 0.00 |
| −V | 5 | Galphimia G | 18.10 | 0.00 | 0.11 | 0.04 | 0.10 |
| −V | 5 | Hist. HC | 6.93 | 0.03 | 0.18 | 0.01 | 0.08 |
| −V | 5 | Oscillococcinum | 17.76 | 0.00 | 0.39 | 0.00 | 0.26 |
| −V | 10 | Sucrets Menthol | 16.75 | 0.00 | 0.36 | 0.06 | 0.17 |
| −V | 10 | Benadryl | 1.09 | 2.91 | 3.15 | 2.24 | 2.07 |
| −V | 1 | Benadryl | 12.59 | 0.18 | 0.29 | 0.00 | 0.08 |

Example 4

Influenza Sensitivity and Specificity

To test whether the POC assay system can correctly type live influenza virus collected from patient, live Hong Kong influenza virus samples were tested. Table 4 shows test results of the assay system on live H5 Hong Kong influenza strain, demonstrating the feasibility and marked improvement in detection capacity over a prior art. Also, Table 5 shows the assay system is far more sensitive than prior art product in detecting Type A influenza.

TABLE 4

| H5 Strains represent H5's Global Spread | Virus Dil | Control | H5 | H1/H3 | Type B | Type A | Call | Titer measured by a prior art (type A only) |
|---|---|---|---|---|---|---|---|---|
| Ck/Malang/BB VET/4/04(Y1) | 1:10 | 8.97 | 39.33 | 0.80 | 0.00 | 45.46 | H5 & A Pos | Pos |
| | 1:100 | 9.65 | 4.70 | 0.35 | 0.21 | 58.60 | H5 & A Pos | Pos |
| | 1:1,000 | 11.10 | 0.95 | 0.60 | 0.23 | 26.30 | A Pos | Wk Pos |
| | 1:10,000 | 13.00 | 0.11 | 0.15 | 0.00 | 2.46 | A Pos | Neg |
| | 1:100,000 | 11.20 | 0.13 | 0.13 | 0.21 | 1.20 | A Pos | neg |
| IDN 5/05 | 1:10 | 8.88 | 34.19 | 0.68 | 0.10 | 36.67 | H5 & A Pos | Pos |
| | 1:100 | 8.95 | 3.42 | 0.19 | 0.00 | 57.72 | H5 & A Pos | Pos |
| | 1:1,000 | 8.72 | 0.59 | 0.58 | 0.51 | 38.84 | A Pos | Pos |
| | 1:10,000 | 19.24 | 0.53 | 0.17 | 0.68 | 1.41 | A Pos | Neg |
| | 1:100,000 | 11.63 | 0.34 | 0.49 | 0.10 | 1.18 | A Pos | Neg |
| Ck/GX/2439/04 | 1:10 | 9.36 | 66.38 | 1.43 | 0.10 | 38.94 | H5 H1/3 & A Pos | Pos |
| | 1:100 | 8.90 | 14.56 | 0.29 | 0.10 | 48.85 | H5 & A Pos | Pos |
| | 1:1,000 | 9.75 | 1.82 | 0.20 | 0.14 | 54.22 | H5 & A Pos | Pos |
| | 1:10,000 | 11.62 | 0.57 | 0.51 | 0.41 | 9.96 | A Pos | Neg |
| | 1:100,000 | 11.58 | 0.24 | 0.16 | 0.20 | 1.97 | A Pos | Neg |
| BhGs/QH/15/05 | 1:10 | 15.27 | 31.86 | 0.56 | 0.04 | 63.35 | H5 & A Pos | Pos |
| | 1:100 | 13.39 | 4.23 | 1.02 | 0.45 | 30.70 | H5 H1/3 & A Pos | Pos |
| | 1:1,000 | 14.80 | 1.01 | 0.73 | 0.21 | 9.51 | H5 & A Pos | Pos |
| | 1:10,000 | 10.45 | 0.44 | 0.47 | 0.17 | 1.03 | A Pos | Neg |
| | 1:100,000 | 11.22 | 0.15 | 0.12 | 0.11 | 0.37 | Neg | Neg |
| Little Egret/HK/718/06 | 1:10 | 5.00 | 6.21 | 0.40 | 0.09 | 46.84 | H5 & A Pos | Pos |
| | 1:100 | 10.91 | 1.45 | 0.10 | 0.07 | 72.28 | H5 & A Pos | Pos |
| | 1:1,000 | 11.82 | 0.19 | 0.16 | 0.11 | 30.92 | A Pos | Wk Pos |
| | 1:10,000 | 7.89 | 0.46 | 0.44 | 0.28 | 6.42 | A Pos | Neg |
| | 1:100,000 | 6.77 | 0.61 | 0.80 | 0.50 | 1.05 | A Pos | Neg |
| Gs/YN/5539/2005 | 1:10 | 7.11 | 1.21 | 0.49 | 0.43 | 41.65 | H5 & A Pos | Pos |
| | 1:100 | 8.68 | 0.52 | 0.23 | 0.12 | 42.22 | A Pos | Pos |
| | 1:1,000 | 11.43 | 0.55 | 0.68 | 0.40 | 48.22 | A Pos | Pos |
| | 1:10,000 | 11.05 | 0.30 | 0.44 | 0.24 | 14.67 | A Pos | Neg |
| | 1:100,000 | 8.91 | 0.30 | 0.26 | 0.13 | 0.99 | Neg | Neg |
| Dk/VNM/N-XX/04 | 1:10 | 9.79 | 5.75 | 0.16 | 0.00 | 47.18 | H5 & A Pos | Pos |
| | 1:100 | 13.81 | 0.83 | 0.82 | 0.50 | 38.98 | A Pos | Pos |
| | 1:1,000 | 12.37 | 0.15 | 0.21 | 0.10 | 10.27 | A Pos | Neg |
| | 1:10,000 | 15.09 | 0.20 | 0.44 | 0.10 | 2.66 | A Pos | Neg |
| | 1:100,000 | 13.48 | 0.00 | 0.00 | 0.00 | 0.73 | Neg | Neg |
| IDN/535/2006 | 1:10 | 8.47 | 8.84 | 0.41 | 0.16 | 37.48 | H5 & A Pos | Pos |
| | 1:100 | 13.70 | 1.12 | 0.90 | 0.67 | 65.85 | H5 & A Pos | Pos |
| | 1:1,000 | 11.29 | 0.40 | 0.41 | 0.29 | 54.92 | A Pos | Pos |
| | 1:10,000 | 13.41 | 0.22 | 0.24 | 0.15 | 16.47 | A Pos | Wk Pos |
| | 1:100,000 | 11.62 | 0.27 | 0.31 | 0.11 | 4.62 | A Pos | Neg |
| MDk/JK2295/2005 | 1:10 | 7.97 | 12.84 | 0.39 | 0.08 | 54.33 | H5 & A Pos | Pos |
| | 1:100 | 10.02 | 2.86 | 0.23 | 0.29 | 39.73 | H5 & A Pos | Wk Pos |
| | 1:1,000 | 8.62 | 0.14 | 0.00 | 0.00 | 6.36 | A Pos | Neg |
| | 1:10,000 | 12.17 | 0.16 | 0.00 | 0.00 | 0.36 | Neg | Neg |
| | 1:100,000 | 13.56 | −0.20 | 0.00 | 0.00 | 0.31 | Neg | Neg |
| DK/ST/4231/03 | 1:10 | 6.15 | 34.04 | 0.61 | 0.00 | 48.24 | H5 & A Pos | Pos |
| | 1:100 | 10.94 | 4.51 | 0.53 | 0.31 | 43.05 | H5 & A Pos | Pos |
| | 1:1,000 | 11.33 | 0.49 | 0.08 | 0.06 | 14.37 | A Pos | Neg |
| | 1:10,000 | 11.18 | 0.00 | 0.13 | −0.05 | 2.01 | A Pos | Neg |
| | 1:100,000 | 12.66 | 0.37 | 0.43 | 0.19 | 0.51 | Neg | Neg |
| Japaneese White Eye/HK/1038/06 | 1:10 | 8.92 | 4.34 | 0.46 | 0.20 | 52.81 | H5 & A Pos | Pos |
| | 1:100 | 10.30 | 0.69 | 0.54 | 0.32 | 28.36 | A Pos | Pos |
| | 1:1,000 | 10.98 | 0.00 | 0.05 | 0.00 | 8.98 | A Pos | Pos |
| | 1:10,000 | 11.37 | −0.03 | 0.21 | 0.00 | 0.98 | Neg | Neg |
| | 1:100,000 | 9.16 | 0.32 | 0.00 | 0.25 | 0.40 | Neg | Neg |
| Ck/HK/YU/22/02 | 1:10 | 8.84 | 69.54 | 1.75 | 0.00 | 33.12 | H5 H1/3 & A Pos | Pos |
| | 1:100 | 14.32 | 10.21 | 0.46 | 0.14 | 52.91 | H5 & A Pos | Pos |
| | 1:1,000 | 12.55 | 1.41 | 0.21 | 0.15 | 40.61 | H5 & A Pos | Pos |
| | 1:10,000 | 11.75 | 0.00 | 0.11 | −0.07 | 7.99 | A Pos | Neg |
| | 1:100,000 | 12.86 | 0.13 | 0.10 | 0.00 | 1.02 | A Pos | Neg |
| Gs/GY/337/2006 | 1:10 | 7.88 | 1.31 | 0.41 | 0.19 | 49.15 | H5 & A Pos | Pos |
| | 1:100 | 10.06 | 0.50 | 0.50 | 0.38 | 64.63 | A Pos | Pos |
| | 1:1,000 | 11.89 | 0.31 | 0.22 | 0.21 | 26.51 | A Pos | Pos |
| | 1:10,000 | 10.79 | 0.22 | 0.37 | 0.16 | 3.68 | A Pos | Neg |
| | 1:100,000 | 12.27 | 0.35 | 0.57 | 0.29 | 0.94 | | Neg |

TABLE 4-continued

| H5 Strains represent H5's Global Spread | Virus Dil | Control | H5 | H1/H3 | Type B | Type A | Call | Titer measured by a prior art (type A only) |
|---|---|---|---|---|---|---|---|---|
| IDN/542/2006 | 1:10 | 7.35 | 35.64 | 0.99 | 0.01 | 31.02 | H5 & A Pos | Pos |
| | 1:100 | 9.29 | 6.31 | 0.30 | 0.08 | 49.08 | H5 & A Pos | Pos |
| | 1:1,000 | 15.86 | 0.55 | 0.35 | 0.43 | 54.28 | A Pos | Pos |
| | 1:10,000 | 13.83 | 0.30 | 0.40 | 0.27 | 16.64 | A Pos | Wk Pos |
| | 1:100,000 | 10.77 | −0.05 | 0.34 | 0.25 | 4.06 | A Pos | Neg |
| Dk/VNM/283/2005 | 1:10 | 7.58 | 27.41 | 0.46 | 0.16 | 50.55 | H5 & A Pos | Pos |
| | 1:100 | 5.46 | 3.64 | 0.47 | 0.24 | 58.40 | H5 & A Pos | Pos |
| | 1:1,000 | 8.33 | 1.13 | 0.94 | 0.55 | 28.40 | H5 & A Pos | Pos |
| | 1:10,000 | 7.04 | 0.34 | 0.48 | 0.30 | 6.03 | A Pos | Neg |
| | 1:100,000 | 8.75 | 0.29 | 0.36 | 0.18 | 1.66 | A Pos | Neg |

TABLE 5

| HA units | Diluition Factor | Mean Fluorscent Units | S/N Ratio | Results from a marketed POC Test product |
|---|---|---|---|---|
| 10 | 0 | 21199.8 | 392 | + |
| 5 | 2 | NT* | N/A | +/− |
| 2.5 | 4 | NT | N/A | Neg |
| 1.25 | 8 | 10488.4 | 194 | NT |
| 1 | 10 | NT | N/A | Neg |
| 0.5 | 20 | 3621.8 | 67 | Neg |
| 0.1 | 100 | 1087.4 | 20 | NT |
| 0.05 | 200 | 532.5 | 10 | NT |
| 0.025 | 400 | 354.4 | 7 | NT |
| 0.0125 | 800 | 86.8 | 2 | NT |
| 0.00625 | 1600 | 90.3 | 2 | NT |
| No Virus or N | N/A | 54.0 | N/A | |

*NT = Not Tested,
Note:
Used A/Texas/1/77

Example 5

Influenza Specificity

To test assay specificity, 40 known influenza negative samples were tested. Table 6 shows the results of this particular study. The detection specificity of 92% and 97.4% was observed.

TABLE 6

| Sample No. | Prior Art | Run 1 | Run 2 |
|---|---|---|---|
| 1 | Neg | Neg | Neg |
| 2 | Neg | Neg | Neg |
| 3 | Neg | Neg | Neg |
| 4 | Neg | Neg | Neg |
| 5 | Neg | Neg | Neg |
| 6 | Neg | Neg | Neg |
| 7 | Neg | Neg | Neg |
| 8 | Neg | Neg | Neg |
| 9 | Neg | Inf. A Pos | Inf. A Pos |
| 10 | Neg | Neg | Neg |
| 11 | Neg | Neg | Neg |
| 12 | Neg | Neg | Neg |
| 13 | Neg | Neg | Neg |
| 14 | Neg | Neg | Inf. B Pos |
| 15 | Neg | Neg | Neg |
| 16 | Neg | Neg | Neg |
| 17 | Neg | Neg | Neg |
| 18 | Neg | Neg | Neg |
| 19 | Neg | Neg | Neg |
| 20 | Neg | Neg | Neg |
| 21 | Neg | Neg | Neg |
| 22 | Neg | Neg | Neg |

TABLE 6-continued

| Sample No. | Prior Art | Run 1 | Run 2 |
|---|---|---|---|
| 23 | Neg | Inf. A Pos | Inf. A Pos |
| 24 | Neg | Neg | Neg |
| 25 | Neg | Neg | Neg |
| 26 | Neg | Neg | Neg |
| 27 | Neg | Neg | Neg |
| 28 | Neg | Neg | Neg |
| 29 | Neg | Neg | Neg |
| 30 | Neg | Neg | Neg |
| 31 | Neg | Neg | Neg |
| 32 | Neg | Neg | Neg |
| 33 | Neg | Neg | Neg |
| 34 | Neg | Neg | Neg |
| 35 | Neg | Neg | Neg |
| 36 | Neg | Neg | Neg |
| 37 | Neg | Neg | Neg |
| 38 | Neg | Neg | Neg |
| 39 | Neg | Neg | Neg |
| 40 | Neg | Neg | Neg |

Example 6

NT-proBNP Detection

Sample comprised recombinant peptide in equine serum (40 μl sample+10 μl reagent). Reagent comprised Europium-conjugated mAb-pRNA 6a6. BSA-pRNA (6b6, supra) was striped on a nitrocellulose membrane dipstick test device (e.g., FIG. 6). In FIG. 6, lanes 1-4 correspond to 0, 10, 100, 1000 peptide at pg/mL; reference no. 5 (FIG. 6A) corresponds to detectable NT-proBNP at 10, 100 and 1000 pg/mL. FIG. 6 demonstrates the sensitivity using a standard curve calibrated using two standards/level to obtain fitted concentration of pg/mL as illustrated in the standard curve provided in FIG. 9. Based on the calibration data the limit of detection was at 1.7 attamoles ($10^{-18}$) or 0.36 pg/mL NT-proBNP. Furthermore, the limit of quantitation was about 5.8 attamoles or 1.23 pg/mL NT-proBNP. Therefore, the systems of the invention can also be used to quantify an analyte and are quite sensitive. The assay was calibrated using two standards/level; algorithm=5PL weighted.

| standard | peptide concentration pg/ml | signal (peak height) RFU | | average RFU | % CV | fitted concentration pg/ml | | average pg/ml |
|---|---|---|---|---|---|---|---|---|
| 1 | 0 | 227 | 222 | 225 | 1.6 | 0.0 | 0.0 | 0.0 |
| 2 | 10 | 3381 | 3449 | 3415 | 1.4 | 9.9 | 10.1 | 10.0 |
| 3 | 50 | 14792 | 14409 | 14601 | 1.9 | 50.7 | 49.1 | 49.9 |
| 4 | 125 | 30408 | 29976 | 30192 | 1.0 | 126.0 | 123.5 | 124.8 |
| 5 | 250 | 47477 | 45495 | 46486 | 3.0 | 265.1 | 243.6 | 254.4 |
| 6 | 500 | 60915 | 60166 | 60540 | 0.9 | 494.8 | 475.9 | 485.4 |
| 7 | 1000 | 73035 | 70788 | 71912 | 2.2 | 1137.5 | 931.2 | 1034.4 |

| signal, RFU | fitted concentration, pg/ml | |
|---|---|---|
| 343 | 0.36 | (limit of detection = concentration corresponding to average signal of 20 reps of 0 + 3SD) |
| 400 | 0.53 | |
| 600 | 1.14 | |
| 629 | 1.23 | (limit of quantitation = concentration corresponding to average signal of 20 reps of 0 + 10SD) |
| 1000 | 2.37 | |

Conclusion

The foregoing examples and data demonstrate that the SCD and Test Device assay system efficiently and effectively identify Type A and Type B influenza strains and are capable of correctly identifying H1, H3, and H5 subtypes. The assay system demonstrated superior performance in comparison to prior art products as measured in terms of influenza detection specificity and sensitivity. As shown in Table 2, the system's specificity for influenza virus was unequivocally demonstrated by showing no false positive signals toward non-influenza virus or bacterial samples. In addition, as shown in table 5, the specificity for influenza detection was 97.4%. In terms of detection sensitivity, test results shown in Table 1 and Table 4 demonstrates detection ability in diluted concentration ranges beyond the capabilities of known prior art systems. For example, H3N2 A/New York/55/2004 influenza A has tissue culture infectious dose (TCID) 50 titer 3.5 at 1:100 dilution (e.g., TCID50 3.5 is $5\times10^3$ infectious virus particles/mL) for the nucleoprotein antigen (A). The detection sensitivity was seen at the 1:10,000 dilution where the signal to cutoff was seen to be 1.88 for a TCID50 titer of approximately 10 TCID50 units/mL for the nucleoprotein antigen (A). A similar end point titer was seen with B/Ohio/15/2001 for the nucleoprotein antigen (B). Furthermore, systems of the invention were capable of detecting viral concentrations of from between about $TCID_{50}$ 10 and about 700, as demonstrated in Table 1. In addition, virus used for testing in Table 6 ranged from TCID 6.7 to 9.1 and the detection sensitivity for these virus ranges from 0.0067 to 0.0097.

What is claimed is:

1. A kit comprising:
   a) a sample collection device having an open end, and comprising;
      i) a sample tube;
      ii) a sample collection implement;
      iii) a dropper cap;
      iv) a compartment comprising an extraction reagent;
   wherein lyophilized immunoreagents are provided in a chamber proximal to the open end or in the dropper cap; and
   b) a test device comprising one or more addressable regions configured for detection of one or more analytes, wherein the kit is for detection of the one or more analytes by immunoassay.

2. The kit of claim 1, wherein said extraction reagent comprises a salt at about 0.75 to about 1.125M in a buffered solution.

3. The kit of claim 1, wherein said extraction reagent comprises saponin at about 1.0% to about 1.5% in a buffered solution.

4. The kit of claim 1, wherein said extraction reagent comprises a zwitterionic agent at about 0.25% to about 0.5% in a buffered solution.

5. The kit of claim 1, wherein said one or more analytes comprises one or more virus or virus components.

6. The kit of claim 5, wherein said virus is influenza A and/or influenza B.

7. The kit of claim 6, wherein said influenza A includes subtypes of a formula HxNy, where x is 1 through 16, and y is 1 through 9, or any combination of xy thereof.

8. The kit of claim 6, wherein said influenza A is H5N1.

9. The kit of claim 5, wherein said dropper cap comprises a plurality of pairs of detection and capture probes.

10. The kit of claim 5, configured to provide a limit of sensitivity for detection of said one or more different analytes of at least about 10 $TCID_{50}$ per mL as measured by tissue culture infectious dose 50 ($TCID_{50}$).

11. The kit of claim 1, wherein said one or more analytes comprises one or more analytes associated with heart damage, heart disease or heart condition.

12. The kit of claim 1, wherein said one or more analytes comprises one or more analytes associated with brain damage, brain disease or brain condition.

13. The kit of claim 1, configured to provide a limit of sensitivity and specificity for detection of said one or more different analytes of at least about 97%.

14. The kit of claim 1, configured to provide a limit of sensitivity for detection of said one or more different analytes of at least about 0.030 pg/ml.

15. The kit of claim 1, configured to provide a limit of sensitivity for detection of said one or more different analytes of at least about 1.5 attomoles.

16. The kit of claim 1, wherein the lyophilized immunoreagents are provided in the chamber proximal to the open end.

17. The kit of claim 16, wherein the immunoreagents comprise one or more pairs of detection and capture probes, and wherein the kit is configured to provide a limit of sensitivity for detection of said one or more different analytes of at least about 0.030 pg/ml.

18. The kit of claim 16, wherein the immunoreagents comprise one or more pairs of probes comprising a detection probe and a capture probe, wherein said one or more pairs of probes is configured to detect one or more different analyte.

19. The kit of claim 1, wherein the lyophilized immunoreagents are provided in the dropper cap.

20. The kit of claim 19, wherein the immunoreagents comprise one or more pairs of detection and capture probes, and wherein the kit is configured to provide a limit of sensitivity for detection of said one or more different analytes of at least about 0.030 pg/ml.

21. The kit of claim 19, wherein the immunoreagents comprise one or more pairs of probes comprising a detection probe and a capture probe, wherein said one or more pairs of probes is configured to detect one or more different analyte.

22. The kit of claim 1, wherein the one or more analyte is a peptide or a protein.

* * * * *